(12) United States Patent
Whitehouse

(10) Patent No.: US 8,796,211 B2
(45) Date of Patent: *Aug. 5, 2014

(54) METHOD OF TREATING CORONARY ARTERY DISEASE FGF-2

(75) Inventor: Martha Jo Whitehouse, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 13/088,132

(22) Filed: Apr. 15, 2011

(65) Prior Publication Data

US 2012/0289464 A1 Nov. 15, 2012

Related U.S. Application Data

(63) Continuation of application No. 10/184,708, filed on Jun. 28, 2002, now abandoned, and a continuation of application No. 09/385,114, filed on Aug. 27, 1999, now Pat. No. 6,440,934.

(60) Provisional application No. 60/104,102, filed on Oct. 13, 1998, provisional application No. 60/104,103, filed on Oct. 13, 1998.

(51) Int. Cl.
*A61K 38/18* (2006.01)

(52) U.S. Cl.
USPC .................................. 514/12; 514/2

(58) Field of Classification Search
None
See application file for complete search history.

(56) References Cited

U.S. PATENT DOCUMENTS

| | | |
|---|---|---|
| 4,296,100 A | 10/1981 | Franco |
| 4,378,347 A | 3/1983 | Franco |
| 4,956,455 A | 9/1990 | Esch et al. |
| 5,137,510 A | 8/1992 | VanDeripe |
| 5,137,734 A | 8/1992 | Spiegelman et al. |
| 5,155,214 A | 10/1992 | Baird et al. |
| 5,155,217 A | 10/1992 | Goldfarb et al. |
| 5,194,596 A | 3/1993 | Tischer et al. |
| 5,213,570 A | 5/1993 | VanDeripe |
| 5,238,916 A | 8/1993 | Goldfarb et al. |
| 5,244,460 A | 9/1993 | Unger et al. |
| 5,269,326 A | 12/1993 | Verrier |
| 5,286,252 A | 2/1994 | Tuttle et al. |
| 5,302,702 A | 4/1994 | Seddon et al. |
| 5,310,883 A | 5/1994 | Seddon et al. |
| 5,314,872 A | 5/1994 | Kato et al. |
| 5,350,836 A | 9/1994 | Kopchick et al. |
| 5,352,589 A | 10/1994 | Bergonzoni et al. |
| 5,371,206 A | 12/1994 | Seddon et al. |
| 5,387,673 A | 2/1995 | Seddon et al. |
| 5,439,818 A | 8/1995 | Fiddes et al. |
| 5,464,774 A | 11/1995 | Baird et al. |
| 5,491,220 A | 2/1996 | Seddon et al. |
| 5,514,566 A | 5/1996 | Fiddes et al. |
| 5,604,293 A | 2/1997 | Fiddes et al. |
| 5,612,211 A | 3/1997 | Wilson et al. |
| 5,750,659 A | 5/1998 | Basilico et al. |
| 5,773,252 A | 6/1998 | Greene et al. |
| 5,792,453 A | 8/1998 | Hammond et al. |
| 5,852,177 A | 12/1998 | Senoo et al. |
| 5,872,226 A | 2/1999 | Nathans et al. |
| 6,440,934 B1 | 8/2002 | Whitehouse |
| 6,451,303 B1 | 9/2002 | Whitehouse |
| 6,653,279 B1 | 11/2003 | Gao |
| 7,112,560 B2 | 9/2006 | Whitehouse |
| 7,511,019 B2 | 3/2009 | Whitehouse et al. |
| 7,541,333 B2 | 6/2009 | Whitehouse |
| 7,858,584 B2 | 12/2010 | Whitehouse et al. |
| 2002/0115603 A1 | 8/2002 | Whitehouse |
| 2002/0165160 A1 | 11/2002 | Whitehouse |

FOREIGN PATENT DOCUMENTS

| | | |
|---|---|---|
| EP | 0 228 449 B1 | 7/1987 |
| WO | WO 86/07595 | 12/1986 |
| WO | WO 87/01728 | 3/1987 |
| WO | WO 89/04832 A1 | 6/1989 |

OTHER PUBLICATIONS

Hasdai et al. (Int'l J. of Cardiology, vol. 59, 1997, pp. 133-138).*
Lee et al. (Arterioscl., Thrombosis & Vascular Biology, 1997, vol. 17, pp. 1859-1867).*
Losordo et al. (Circulation, vol. 98, pp. 2800-2804, 1998).*
Cao et al. (Nature Medicine, May 2003, vol. 9, No. 5, pp. 603-613).*
Abraham et al. (1986), "Human Basic Fibroblast Growth Factor: Nucleotide Sequence and Genomic Organization," *The EMBO Journal* 5:2523-2528.
Anderson (1994), "Gene Therapy for Genetic Diseases," *Human Gene Therapy* 5:281-282.
Banai et al. (1994), "Angiogenic-Induced Enhancement of Collateral Blood Flow to Ischemic Myocardium by Vascular Endothelial Growth Factor in Dogs," *Circulation* 89:2183-2189.
Barinaga (1994), "Step Taken Toward Improved Vectors for Gene Transfer," *Science* 266:1326.
Barr (1994), "Efficient Catheter-Mediated Gene Transfer into the Heart Using Replication-Defective Adenovirus," *Gene Therapy* 1:51-58.
Battler et al. (1993), "Intracoronary Injection of Basic Fibroblast Growth Factor Enhances Angiogenesis in Infarcted Swine Myocardium," *JACC* 22:2001-2006.

(Continued)

*Primary Examiner* — Hope Robinson
(74) *Attorney, Agent, or Firm* — Alston & Bird LLP

(57) ABSTRACT

The present invention provides a unit dose composition comprising 0.2 µg/kg to 48 µg/kg of an FGF-2 of SEQ ID NO:2, or an angiogenically active fragment or mutein thereof in a pharmaceutically acceptable carrier. Also provided is a method for treating a human patient for coronary artery disease, comprising administering into one or more coronary vessels or a peripheral vein of said patient a safe and angiogenically effective dose of a recombinant FGF-2, or an angiogenically active fragment or mutein thereof. Also provided is a pharmaceutical composition comprising a therapeutically effective amount of FGF-2, alone or in combination with heparin, in a therapeutically effective carrier.

28 Claims, 5 Drawing Sheets

(56) References Cited

OTHER PUBLICATIONS

Benjamin et al. (1998), "A Plasticity Window for Blood Vessel Remodelling is Defined by Pericyte Coverage of the Preformed Endothelial Network and is Regulated by PDGF-B and VEGF," *Development* 125:1591-1598.

Bikfalvi et al. (1997), "Biological Roles of Fibroblast Growth Factor-2," *Endocrine Reviews* 18:26-45.

Brown (1995), "Gene Therapy 'Ovesold' by Researchers, Journalists," *The Washington Post*: A1 and A22.

Bork et al. (1996), "Go Hunting in Sequence Databases but Watch Out for the Traps," *Trends in Genetics* 12:425-427.

Bork (2000), "Powers and Pitfalls in Sequence Analysis: The 70% Hurdle," *Genome Research* 10:398-400.

Brenner (1999), "Errors in Genome Annotation," *Trends in Genetics* 15:132-133.

Burgess et al. (1989), "The Heparin-Binding (Fibroblast) Growth Factor Family of Proteins," *Annu. Rev. Biochem.* 58:575-606.

Challita et al. (1994), "Lack of Expression from a Retroviral Vector After Transduction of Murine Hematopoietic Stem Cells is Associated with Methylation in vivo," *Proc. Natl. Acad. Sci. USA* 91:2567-2571.

Clements et al. (1993), "Activation of Fibroblast Growth Factor (FGF) Receptors by Recombinant Human FGF-5," *Oncogene* 8:1311-1316.

Coghlan (1995), "Gene Dream Fades Away," *New Scientist* 148:14-15.

Corallini et al. (1996), "Promotion of Tumour Metastases and Induction of Angiogenesis by Native HIV-1 Tat Protein from BK Virus/Tat Transgenic Mice," *AIDS* 10:701-710.

Coulier et al. (1991), "Putative Structure of the FGF6 Gene Product and Role of the Signal Peptide," *Oncogene* 6:1437-1444.

Doerks et al. (1998), "Protein Annotation: Detective Work for Function Prediction," *Trends in Genetics* 14:248-250.

Fisher et al. (1997), "Recombinant Adeno-Associated Virus for Muscle Directed Gene Therapy," *Nature Medicine* 3:306-312.

Folkman (1998), "Angiogenic Therapy of the Human Heart," *Circulation* 97:628-629.

Galzie et al. (1997), "Fibroblast Growth Factors and Their Receptors," *Biochem. Cell. Biol.* 75:669-685.

Giordano et al. (1995), "Reduced Myocardial Ischemia after Recombinant Adenovirus Mediated In-Vivo Fibroblast Growth Factor-5 Gene Transfer," *J. Invest. Med.* 3:278A.

Giordano et al. (1996), "Intracoronary Gene Transfer of Fibroblast Growth Factor-5 Increases Blood Flow and Contractile Function in an Ischemic Region of the Heart," *Nature Medicine* 2:534-539.

Guo et al. (2004), "Protein Tolerance to Random Amino Acid Changes," *Proc. Natl. Acad. Sci., U.S.A.* 101(25):9205-9210.

Guzman et al. (1993), "Efficient Gene Transfer into Myocardium by Direct Injection of Adenovirus Vectors," *Circulation Research* 73:1202-1207.

Harada et al. (1994), "Basic Fibroblast Growth Factor Improves Myocardial Function in Chronically Ischemic Porcine Hearts," *J. Clin. Invest.* 94:623-630.

Hasegawa et al.. (1999), "Basic Fibroblast Growth Factor Increases Regional Myocardial Blood Flow and Salvages Myocardium in the Infarct Border Zone in a Rabbit Model of Acute Myocardial Infarction," *The Journal of Vascular Diseases* 50(6): 487-495.

Isner (1996) "The Role of Angiogenic Cytokines in Cardiovascular Disease," *Clinical Immunology and Immunopathology* 80:S82-S91.

Jaroff (1996), "Keys to the Kingdom," *Time* 148:24-29.

Kass-Eisler et al. (1993), "Quantitative Determination of Adenovirus-Mediated Gene Delivery to Rat Cardiac Myocytes in vitro and in vivo," *Proc. Natl. Acad. Sci. USA* 90:11498-11502.

Kirschner et al. (1995), "Basic Fibroblast Growth Factor Protects Against Excitotoxicity and Chemical Hypoxia in Both Neonatal and Adults Rats," *J. Cerebral Blood Flow and Metabolism* 15:619-623.

Klagsbrun (1991), "Angiogenic Factors: Regulators of Blood Supply-Side Biology," *The New Biologist* 3:745-749.

Laham et al. (1998), "Local Perivascular Basic Fibroblast Growth Factor (bFGF) Treatment in Patients with Ischemic Heart Disease," *J. Am. Coll. Cardiol.* 31:394A.

Laham et al. (2000), "Intrapericardial Delivery of Fibroblast Growth Factor-2 Induces Neovascularization in a Porcine Model of Chronic Myocardial Ischemia," *The Journal of Pharmacology and Experimental Therapeutics* 292:795-802.

Landau et al. (1995), "Intrapericardial Basic Fibroblast Growth Factor Induces Myocardial Angiogenesis in a Rabbit Model of Chronic Ischemia," *American Heart Journal* 129:924-931.

Lazarous et al. (1996), "Comparative Effects of Basic Fibroblast Growth Factor and Vascular Endothelial Growth Factor on Coronary Collateral Development and the Arterial Response to Injury," *Circulation* 94:1075-1082.

Lazarous et al. (1995), "Effects of Chronic Systemic Administration of Basic Fibroblast Growth Factor on Collateral Development in the Canine Heart," *Circulation* 91:145-153.

Lipton et al. (1988), "Acidic Fibroblast Growth Factor Enhances Regeneration of Processes by Postnatal Mammalian Retinal Ganglion Cells in Culture," *Proc. Natl. Acad. Sci., USA* 85:2388-2392.

Lopez et al. (1996), "Local Perivascular Administration of Basic Fibroblast Growth Factor: Drug Delivery and Toxicological Evaluation," *Drug and Metabolism and Disposition* 24:922-924.

Magovern et al. (1996), "Direct in vivo Gene Transfer to Canine Myocardium Using a Replication-Deficient Adenovirus Vector," *Ann. Thorac. Surg.* 62:425-434.

Marshall (1995), "Gene Therapy's Growing Pains," *Science* 269:1050-1055.

Massague et al. (1987), "The TGF-beta Family of Growth and Differentiation Factors," *Cell* 49:437-438.

Mathieu et al. (1995), "Receptor Binding and Mitogenic Properties of Mouse Fibroblast Growth Factor 3," *the Journal of Biological Chemistry* 270:24197-24203.

Miyamoto et al. (1993), "Molecular Cloning of a Novel Cytokine cDNA Encoding the Ninth Member of the Fibroblast Growth Factor Family, Which Has a Unique Secretion Property," *Molecular and Cellular Biology* 13:4251-4259.

Miyataka et al. (1998), "Basic Fibroblast Growth Factor Increased Regional Myocardial Blood Flow and Limited Infarct Size of Acutely Infarcted Myocardium in Dogs," *Angiology* 49:381-390.

Nabel et al. (1993), "Recombinant Fibroblast Growth Factor-1 Promotes Intimal Hyperplasia and Angiogenesis in Arteries In Vivo," *Nature* 362:844-846.

Nahreinei et al. (1993), "Versatile Adeno-Associated Virus 2-Based Vectors for Construction Recombinant Virions," *Gene* 124:257-262.

Ngo et al. (1994), "Computational Complexity, Protein Structure Prediction, and the Levinthal Paradox," *The Protein Folding Problem and Tertiary Structure Prediction*, pp. 492-495.

Ohno et al. (1994), "Gene Therapy for Vascular Smooth Muscle Cell Proliferation After Arterial Injury," *Science* 265:781-784.

Orkin et al. (Dec. 7, 1995), "Report and Recommendations of the Panel to Assess the HIB Investment in Research on Gene Therapy," 41 pages.

Ornitz et al. (1996), "Receptor Specificity of the Fibroblast Growth Factor Family," *J. Biol. Chem.* 271:15292-15297.

Pilbeam et al. (1993) "Comparison of the Effects of Various Lengths of Synthetic Human Parathyroid Hormone—Related Peptide (hPTHrP) of Malignancy on Bone Resorption and formation in Organ Culture," *Bone* 14:717-720.

Rakusan (1995), "Coronary Angiogenesis," *Annals New York Academy of Sciences* 752:257-265.

Rubin et al. (1989), "Purification and Characterization of a Newly Identified Growth Factor Specific for Epithelial Cells," *Proc. Natl. Acad. Sci. USA* 86:802-806.

Schubert et al. (1987), "Multiple Influences of a Heparin-Binding Growth Factor on Neuronal Development," *The Journal of Cell Bioloby* 104:635-643.

Schumacher et al. (1997), "Induction of Neoangiogenesis in Ischemic Myocardium by Human Growth Factors," *Circulation* 97:645-650.

Sellke et al. (1994), "Basic FGF Enhances Endothelium-Dependent Relaxation of the Collateral-Perfused Coronary Microcirculation," *The American Physiological Society* 267:H1303-H1311.

(56) References Cited

OTHER PUBLICATIONS

Sellke et al. (1996), "Enhanced Microvascular Relaxations to VEGF and bFGF in Chronically Ischemic Porcine Myocardium," *Am. J. Physiol.* 271:H713-H720.
Sellke et al. (1996), "Angiogenesis Induced by Acidic Fibroblast Growth Factor as an Alternative Method of Revascularization for Chronic Myocardial Ischemia," *Surgery* 120:182-188.
Sellke et al. (1998), "Therapeutic Angiogenesis with Basic Fibroblast Growth Factor: Technique and Early Results," *The Society of Thoracic Surgeons* 65:1540-1544.
Shou et al. (1997), "Effect of Basic Fibroblast Growth Factor on Myocardial Angiogenesis in Dogs with Mature Collateral Vessels," *JACC* 29:1102-1106.
Simons et al. (2002), "Pharmacological Treatment of Coronary Artery Disease with Recombinant Fibroblast Growth Factor-2: Double-Blind, Randomized, Controlled Clinical Trial," *Circulation* 105:788-793.
Skolnick et al. (2000), "From Genes to Protein Structure and Function: Novel Applications of Computational Approaches in the Genomic Era," *Trends in Biotech* 18:34-39.
Slavin (1995), "Fibroblast Growth Factors: At the Heart of Angiogenesis," *Cell Biology International* 19:431-444.
Smith et al. (1997), "The Challenges of Genome Sequence Annotation or 'The Devil is in the Details'," *Nature Biotech* 15:1222-1223.
Uchida et al. (1995), "Angiogenic Therapy of Acute Myocardial Infarction by Intrapericardial Injection of Basic Fibroblast Growth Factor and Heparin Sulfate: An Experimental Study," *American Heart Journal* 130:1182-1188.
Udelson et al. (2000), "Therapeutic Angiogenesis with Recombinant Fibroblast Growth Factor-2 Improves Stress and Rest Myocardial Perfusion Abnormalities in Patients with Severe Symptomatic Chronic Coronary Artery Disease," *Circulation* 102:1605-1610.
Unger et al. (1994), "Basic Fibroblast Growth Factor Enhances Myocardial Collateral Flow in a Canine Model," *Am. J. Physiol* 266:H1588-H1595.
Valles et al. (1990), "Acidic Fibroblast Growth Factor is a Modulator of Epithelial Plasticity in a Rat Bladder Carcinoma Cell Line," *Proc. Natl. Acad. Sci. USA* 87:1124-1128.
Vukicevic et al. (1996), "Induction of Nephrogenic Mesenchyme by Osteogenic Protein 1 (Bone Morphogenetic Protein 7)," *Proc. Natl. Acad. Sci. USA* 93:9021-9026.
Watanabe et al. (1998), "Effect of Basic Fibroblast Growth Factor on Angiogenesis in the Infarcted Porcine Heart," *Basic Res. Cardiol.* 93:30-37.
Wells (1990), "Additivity of Mutational Effects in Proteins," *Biochemistry* 29:8509-8517.
Xiao et al. (1996), "Efficient Long-Term Gene Transfer into Muscle Tissue of Immunocompetent Mice by Adeno-Associated Virus Vector," *Journal of Virology* 70:8098-8108.
Yanagisawa-Miwa et al. (1992), "Salvage of Infarcted Myocardium by Angiogenic Action of Basic Fibroblast Growth Factor," *Science* 257:1401-1403.
Yayon et al. (1990), "Autocrine Regulation of Cell Growth and Transformation by Basic Fibroblast Growth Factor," *Cancer and Metastasis Reviews* 9:191-202.

Baird et al.(1988), "Receptor- and Heparin-Binding Domains of Basic Fibroblast Growth Factor," *Proceedings of the National Academy of Sciences* 85:2324-2328.
Eriksson et al. (1991), "Three-Dimensional Structure of Human Basic Fibroblast Growth Factor," *Proceedings of the National Academy of Sciences* 88:3441-3445.
Fox et al. (1988), "Production, Biological Activity, and Structure of Recombinanat Basic Fibroblast Growth Factor and an Analog with Cysteine Replaced by Serine," *The Journal of Biological Chemistry* 263 (34): 18452-18458.
Heath et al. (1991), "Mutations in the Heparin-Binding Domains of Human Basic Fibroblast Growth Factor Alter Its Biological Activity," *Biochemistry* 30:5608-5615.
Lopez et al. (1997), "Basic Fibroblast Growth Factor in a Porcine Model of Chronic Myocardial Ischemia: A Comparison Angiographic, Echocardiographic and Coronary Flow Parameters," *The Journal of Pharmacology and Experimental Therapeutics* 282 (1): 385-390.
Presta et al. (1992), "Structure-Function Relationship of Basic Fibroblast Growth Factor: Site-Directed Mutagenesis of a Putative Heparin-Binding and Receptor-Binding Region," *Biochemical and Biophysical Research Communication* 185 (3): 1098-1107.
Presta et al. (1993), "Subcellular Localization and Biological Activity of Mr 18,000 Basic Fibroblast Growth Factor: Site-Directed Mutagenesis of a Putative Nuclear Translocation Sequence," *Growth Factors* 9:269-278.
Seno et al. (1988), "Stabilizing Basic Fibroblast Growth Factor Using Protein Engineering," *Biochemical and Biophysical Research Communications* 151 (2): 701-708.
Springer et al. (1994), "Identification and Concerted Function of Two Receptor Binding Surfaces on Basic Fibroblast Growth Factor Required for Mitogenesis," *The Journal of Biological Chemistry* 269 (43): 26879-26884.
Thompson et al. (1994), "Energetic Characterization of the Basic Fibroblast Growth Factor-Heparin Interaction: Identification of the Heparin Binding Domain," *Biochemistry* 33: 3831-3840.
Yoshida et al. (1987), "Genomic Sequence of *hst*, a Transforming Gene Encoding a Protein Homologous to Fibroblast Growth Factors and the *int*-2-Encoded Protein," *Proceedings of the National Academy of Sciences* 84:7305-7309.
Zhang et al. (1991), "Three-Dimensional Structure of Human Basic Fibroblast Growth Factor, a Structural Homolog of Interleukin 1β," *Proceedings of the National Acadmey of Sciences* 88:3446-3450, and corrected p. 5477.
Zhu et al. (1991), "Three-Dimensional Structures of Acidic and Basic Fibroblast Growth Factors," *Science* 251: 90-93.
Zhu et al. (1995), "Glu-96 of Basic Fibroblast Growth Factor Is Essential for High Affinity Receptor Binding," *The Journal of Biological Chemistry* 270 (37): 21869-21874.
Zhu et al. (1997), "Analysis of High-Affinity Binding Determinants in the Receptor Binding Epitope of Basic Fibroblast Growth Factor," *Protein Engineering* 10 (4): 417-421.
Zhu et al. (1998), "Identification of Two New Hydrophobic Residues on Basic Fibroblast Growth Factor Important for Fibroblast Growth Factor Receptor Binding," *Protein Engineering* 11 (10): 937-940.

* cited by examiner

Mean rFGF Plasma Concentration Versus Time Post 1C Administration

Mean rFGF-2 Plasma Concentration-Time Profiles Following IV Administration. Mean rFGF-2 Plasma Concentration Profile Following Administration of 36µg/kg 1C Included for Comparison.

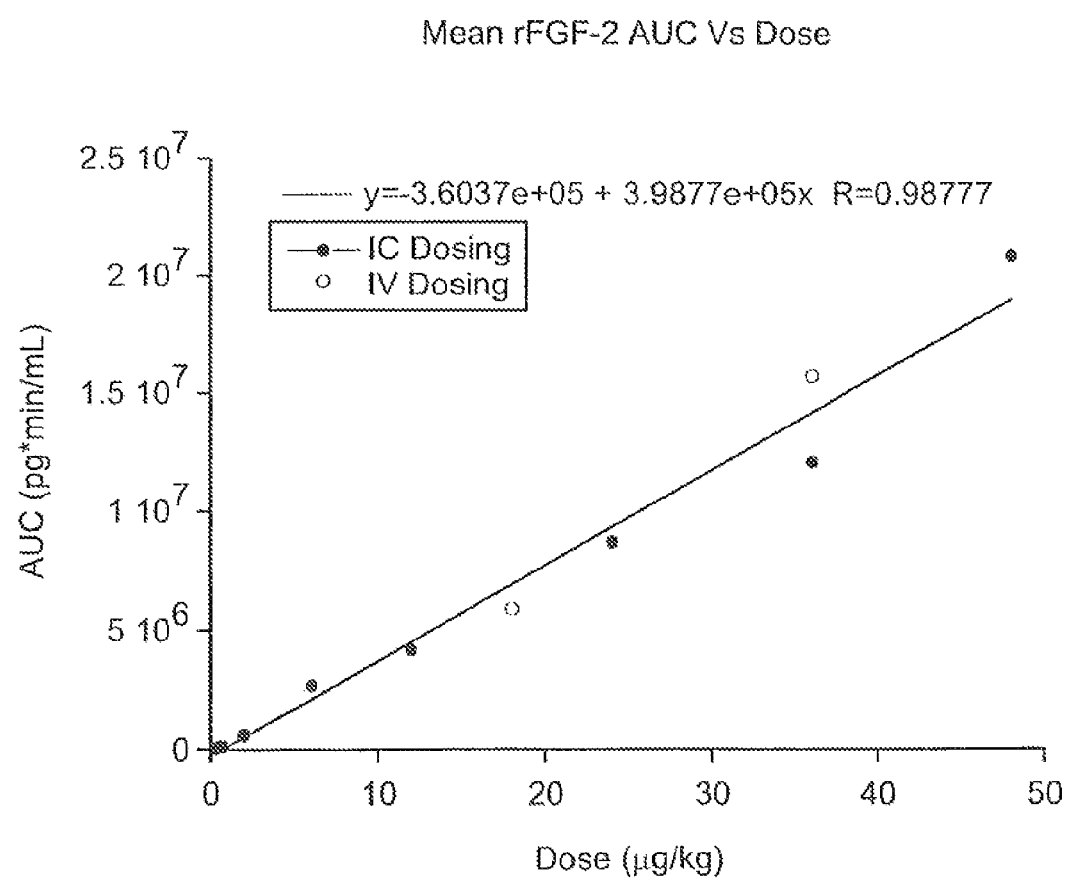

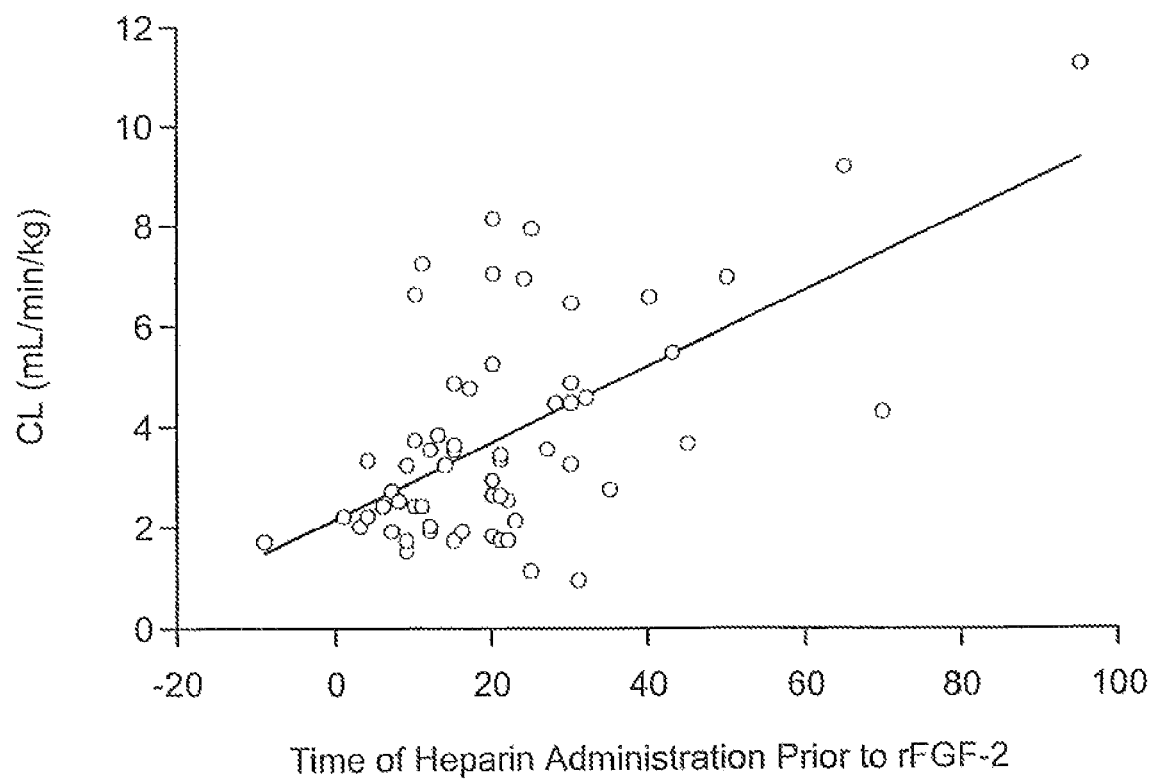

Individual Patient rFGF-2 Dose-Normalized AUC
Versus Dose in Study CS-FG001

SEQUENCE LISTING

```
<160> NUMBER OF SEQ ID NOS: 3

<210> SEQ ID NO 1
<211> LENGTH: 442
<212> TYPE: DNA
<213> ORGANISM: Bovis bovinus
<220> FEATURE:
<221> NAME/KEY: CDS
<222> LOCATION: (1)..(438)

<400> SEQUENCE: 1 cca gcc cta cca gaa gat ggg ggg tcc ggg gcc ttc cca cca ggg cac        48
Pro Ala Leu Pro Glu Asp Gly Gly Ser Gly Ala Phe Pro Pro Gly His
 1               5                  10                  15 ttc aaa gat cca aaa cga cta tat tgt aaa aac ggg ggg ttc ttc cta        96
Phe Lys Asp Pro Lys Arg Leu Tyr Cys Lys Asn Gly Gly Phe Phe Leu
                20                  25                  30 cga atc cac cca gat ggg cga gta gat ggg gta cga gaa aaa tcc gat       144
Arg Ile His Pro Asp Gly Arg Val Asp Gly Val Arg Glu Lys Ser Asp
            35                  40                  45 cca cac atc aaa cta caa cta caa gcc gaa gaa cga ggg gta gta tcc       192
Pro His Ile Lys Leu Gln Leu Gln Ala Glu Glu Arg Gly Val Val Ser
        50                  55                  60 atc aaa ggg gta tgt gcc aac cga tat cta gcc atg aaa gaa gat ggg       240
Ile Lys Gly Val Cys Ala Asn Arg Tyr Leu Ala Met Lys Glu Asp Gly
    65                  70                  75                  80 cga cta cta gcc tcc aaa tgt gta acc gat gaa tgt ttc ttc ttc gaa       288
Arg Leu Leu Ala Ser Lys Cys Val Thr Asp Glu Cys Phe Phe Phe Glu
                85                  90                  95 cga cta gaa tcc aac aac tat aac acc tat cga tcc cga aaa tat tcc       336
Arg Leu Glu Ser Asn Asn Tyr Asn Thr Tyr Arg Ser Arg Lys Tyr Ser
               100                 105                 110 tcc tgg tat gta gcc cta aaa cga acc ggg caa tat aaa cta ggg cca       384
```

```
Ser Trp Tyr Val Ala Leu Lys Arg Thr Gly Gln Tyr Lys Leu Gly Pro
        115                 120                 125 aaa acc ggg cca ggg caa aaa gcc atc cta ttc cta cca atg tcc gcc    432
Lys Thr Gly Pro Gly Gln Lys Ala Ile Leu Phe Leu Pro Met Ser Ala
    130                 135                 140 aaa tcc taag                                                        442
Lys Ser
145

<210> SEQ ID NO 2
<211> LENGTH: 146
<212> TYPE: PRT
<213> ORGANISM: Bovis bovinus

<400> SEQUENCE: 2

Pro Ala Leu Pro Glu Asp Gly Gly Ser Gly Ala Phe Pro Pro Gly His
  1               5                  10                  15

Phe Lys Asp Pro Lys Arg Leu Tyr Cys Lys Asn Gly Gly Phe Phe Leu
             20                  25                  30

Arg Ile His Pro Asp Gly Arg Val Asp Gly Val Arg Glu Lys Ser Asp
         35                  40                  45

Pro His Ile Lys Leu Gln Leu Gln Ala Glu Arg Gly Val Val Ser
     50                  55                  60

Ile Lys Gly Val Cys Ala Asn Arg Tyr Leu Ala Met Lys Glu Asp Gly
 65                  70                  75                  80

Arg Leu Leu Ala Ser Lys Cys Val Thr Asp Glu Cys Phe Phe Phe Glu
             85                  90                  95

Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
        115                 120                 125

Lys Thr Gly Pro Gly Gln Lys Ala Ile Leu Phe Leu Pro Met Ser Ala
    130                 135                 140

Lys Ser
145

<210> SEQ ID NO 3
<211> LENGTH: 9
<212> TYPE: PRT
<213> ORGANISM: Bovis bovinus

<400> SEQUENCE: 3

Met Ala Ala Gly Ser Ile Thr Thr Leu
  1               5
```

METHOD OF TREATING CORONARY ARTERY DISEASE FGF-2

CROSS-REFERENCE TO RELATED APPLICATIONS

This application is a continuation application of U.S. application Ser. No. 10/184,708, filed Jun. 28, 2002 (the content of which is herein incorporated by reference in its entirety), now abandoned, which is a continuation application of U.S. application Ser. No. 09/385,114, filed Aug. 27, 1999 (the content of which is herein incorporated by reference in its entirety), now U.S. Pat. No. 6,440,934, issued Aug. 27, 2002, which claims the benefit of U.S. Provisional Application Ser. No. 60/104,102, filed Oct. 13, 1998 and U.S. Provisional Application Ser. No. 60/104,103, filed Oct. 13, 1998.

FIELD OF THE INVENTION

The present invention is directed to a unit dose composition for inducing cardiac angiogenesis in a human comprising a therapeutically effective amount FGF-2 or an angiogenically active fragment or mutein thereof. The present invention is also directed to a method for administering a single unit dose composition to a human to induce cardiac angiogenesis while minimizing systemic risk to the patient. The present invention is useful because the disclosed unit dose composition, and method for its administration, provide an alternative to angioplasty or surgical intervention for the treatment of coronary artery disease (CAD) and further provide an adjunct for reducing post myocardial infarct (MI) injury in humans.

BACKGROUND OF THE INVENTION

The fibroblast growth factors (FGF) are a family of at least eighteen structurally related polypeptides (named FGF-1 to FGF-18) that are characterized by a high degree of affinity for proteoglycans, such as heparin. The various FGF molecules range in size from 15-23 kD, and exhibit a broad range of biological activities in normal and malignant conditions including nerve cell adhesion and differentiation [Schubert et al., *J. Cell Biol.* 104:635-643 (1987)]; wound healing [U.S. Pat. No. 5,439,818 (Fiddes)]; as mitogens toward many mesodermal and ectodermal cell types, as trophic factors, as differentiation inducing or inhibiting factors [Clements, et al., *Oncogene* 8:1311-1316 (1993)]; and as an angiogenic factor [Harada, *J. Clin. Invest.*, 94:623-630 (1994)]. Thus, the FGF family is a family of pluripotent growth factors that stimulate to varying extents fibroblasts, smooth muscle cells, epithelial cells and neuronal cells.

When FGF is released by normal tissues, such as in fetal development or wound healing, it is subject to temporal and spatial controls. However, many of the members of the FGF family are also oncogenes. Thus, in the absence of temporal and spatial controls, they have the potential to stimulate tumor growth by providing angiogenesis.

Coronary artery disease is a progressive condition in humans wherein one or more coronary arteries gradually become occluded through the buildup of plaque (atherosclerosis). The coronary arteries of patients having this disease are often treated by balloon angioplasty or the insertion of stents to prop open the partially occluded arteries. Ultimately, many of these patients are required to undergo coronary artery bypass surgery at great expense and risk. It would be desirable to provide such patients with a medicament that would enhance coronary blood flow so as to reduce the need to undergo bypass surgery.

An even more critical situation arises in humans when a patient suffers a myocardial infarction, wherein one or more coronary arteries or arterioles becomes completely occluded, such as by a clot. There is an immediate need to regain circulation to the portion of the myocardium served by the occluded artery or arteriole. If the lost coronary circulation is restored within hours of the onset of the infarction, much of the damage to the myocardium that is downstream from the occlusion can be prevented. The clot-dissolving drugs, such as tissue plasminogen activator (tPA), streptokinase, and urokinase, have been proven to be useful in this instance. However, as an adjunct to the clot dissolving drugs, it would also be desirable to also obtain collateral circulation to the damaged or occluded myocardium by angiogenesis.

Accordingly, it is an object of the present invention to provide a medicament and a mode of administration that provides human patients with cardiac angiogenesis during coronary artery disease and/or post acute myocardial infarction. More particularly, it is a further object of the present invention to provide a therapeutic dose of an FGF and a mode of administration to humans that provide the desired property of cardiac angiogenesis, while minimizing adverse effects.

Many of the various FGF molecules have been isolated and administered to various animal models of myocardial ischemia with varying and often times opposite results. According to Battler et al., "the canine model of myocardial ischemia has been criticized because of the abundance of naturally occurring collateral circulation, as opposed to the porcine model, which 'excels' in its relative paucity of natural collateral circulation and its resemblance to the human coronary circulation." Battler et al., "*Intracoronary Injection of Basic Fibroblast Growth Factor Enhances Angiogenesis in Infarcted Swine Myocardium,*" *JACC*, 22(7): 2001-6 (December 1993) at page 2002, col. 1. However, Battler et al., who administered bovine bFGF (i.e., FGF-2) to pigs in a myocardial infarct model, considered the varying results that are obtained from one animal species to another, and expressly discloses that the divergent results "thus emphasiz[e] the caution that must be exercised in extrapolating results from different animal models." Battler et al., at page 2005, col. 1. Further, Battler points out that "the dosage and mode of administration of bFGF [i.e., bovine FGF-2] may have profound implications for the biologic effect achieved." Battler, et al., at page 2005, col. 1. Thus, it is a further object of this invention to discover a dosage and a mode of administration of a fibroblast growth factor that would provide for the safe and efficacious treatment of CAD and/or post MI injury in a human patient. More generally, it is an object of the present invention to provide a pharmaceutical composition and method for inducing angiogenesis in a human heart.

SUMMARY OF THE INVENTION

The Applicants have discovered that administering a single unit dose of about 0.2 µg/kg to about 48 µg/kg of rFGF-2 or an angiogenically active fragment or mutein thereof into one or more coronary vessels (IC) or a peripheral vein (IV) of a human patient in need of coronary angiogenesis, unexpectedly provided the human patient with a rapid and therapeutic coronary angiogenesis that resulted in an unexpectedly large increase (i.e., 96 and 100 seconds of increase in the mean change from baseline for all groups at 2 and 6 months) in the treated patient's exercise tolerance time (ETT) that persisted for an unexpectedly long duration (i.e., 6 months as of this writing). These changes should result in a decreased need for standard revascularization procedures. By the term "coronary angiogenesis," as used herein, is meant the formation of new blood vessels, ranging in size from capillaries to arterioles which act as collaterals in coronary circulation. By way of comparison, angioplasty is considered a therapeutic success if it provides an increase in a patient's ETT of greater than 30 seconds compared to the placebo.

Accordingly, in one aspect, the invention is directed to a unit dose of rFGF-2 comprising a safe and therapeutically effective amount of rFGF-2 or an angiogenically active fragment or mutein thereof. Typically, the safe and therapeutically effective amount comprises about 0.2 µg/kg to about 48 µg/kg of rFGF-2 or an angiogenically active fragment or mutein thereof, based upon ideal body weight. In other embodiments, the safe and therapeutically effective amount of the unit dose comprises 0.2 µg/kg to 2.0 µg/kg, greater than 2.0 µg/kg to less than 24 µg/kg, or 24 µg/kg to 48 µg/kg IC of rFGF-2 or an angiogenically active fragment or mutein thereof. In another embodiment, the safe and therapeutically effective amount of the unit dose comprises 18 µg/kg to 36 µg/kg IV of rFGF-2 or an angiogenically active fragment or mutein thereof. Expressed in absolute terms, the unit dose of the present invention comprises 0.008 mg to 7.2 mg, more typically 0.3 mg to 3.5 mg, of FGF-2 or an angiogenically active fragment or mutein thereof. A suitable FGF-2 is the rFGF-2 of SEQ ID NO:2 or an angiogenically active fragment or mutein thereof.

In another aspect, the present invention is directed to a method of treating a human patient for CAD or to induce coronary angiogenesis therein. The method comprises administering into one or more coronary vessels or a peripheral vein of a human patient in need of treatment for coronary artery disease (or in need of angiogenesis) a safe and therapeutically effective amount of a recombinant FGF-2 (rFGF-2) or an angiogenically active fragment or mutein thereof. Typically, a portion of the safe and therapeutically effective amount is administered to each of two coronary vessels. The safe and therapeutically effective amount comprises about 0.2 µg/kg to about 48 µg/kg of rFGF-2 or an angiogenically active fragment or mutein thereof in a pharmaceutically acceptable carrier. In other embodiments, the safe and therapeutically effective amount comprises 0.2 µg/kg to 2 µg/kg, >2 µg/kg to <24 µg/kg, or 24 µg/kg to 48 µg/kg of rFGF-2 an angiogenically active fragment or mutein thereof in a pharmaceutically acceptable carrier. In absolute terms, the amount of rFGF-2 or angiogenically active fragment or mutein thereof that is used in the above method comprises 0.008 mg to 7.2 mg, more typically 0.3 mg to 3.5 mg of rFGF-2 or an angiogenically active fragment or mutein thereof.

Because FGF-2 is a glycosoaminoglycan (e.g., heparin) binding protein and the presence of a glycosoaminoglycan optimizes activity and AUC (see FIGS. 3 and 4), the IC dosages of RFGF-2 of the present invention typically are administered from 0-30 minutes prior to the administration of a glycosoaminoglycan, such as a heparin. The heparin is administered IC or IV, typically IV. Optionally, the heparin is combined with the unit dose composition.

Because rFGF-2 releases nitric oxide, which is a potent vasodilator, aggressive fluid management prior to (proactively) and during the infusion is critical to patient's safety. Administration of IV fluids (e.g., 500-1000 mL of normal saline) to establish a wedge pressure of 12 mm Hg prior to infusion and administration of boluses of IV fluids (e.g., 200 mL normal saline) for decreases of systolic blood pressure (e.g., <90 mm Hg) associated with infusion optimized the safety of administration of rFGF-2 by IC or IV infusion to human patients.

Because EDTA is a potent chelator of calcium that is required for normal myocardial contraction and cardiac conduction, minimizing the concentration of EDTA is critical to patient's safety. A concentration of EDTA less than 100 :g/ml in the unit dose composition optimized the safety of administration of rFGF-2 by IC or IV infusion to human patients.

Because a sudden bolus of rFGF-2 is associated with profound hypotension in animals, the rate of infusion is critical to patient's safety. Administration at 0.5 to 2 mL per minute, typically 1 mL per minute, optimized the safety of administration of rFGF-2 by IC or IV infusion to human patients.

The unexpected magnitude and duration of the therapeutic benefit that was provided to human patients in need of coronary angiogenesis by the unit dose composition and method of administration was seen as early as two weeks after the single unit dose was administered, and persisted for 6 months after the single unit dose was administered IC or IV, as determined by measuring art-recognized clinical endpoints such as ETT, the "Seattle Angina Questionnaire" (SAQ) and MRI of the target areas of the heart. In particular, when the ETT of 58 human CAD patients was assessed by treadmill at baseline, and at 1 month, 2 months, and 6 months after administration of a single unit dose of rFGF-2 by IC or IV routes, clinical benefit was observed in some patients in all dosage groups. See Table 1. Increases in exercise capacity appear between 1 and 2 months. The mean ETT increased to greater than 60 seconds at 2 and 6 months with greater benefit being seen in the higher dose group (24-48 µg/kg) than in the mid (6-12 µg/kg) or low (0.33-2.0 µg/kg) dose groups. (See Table 1.) Particularly unexpected and unpredicted by animal models, were the mean increases in ETT in human patients of 93.4 and 87.5 seconds that were observed at 2 and 6 months, respectively, post-dosing for those patients administered a unit dose of rFGF-2 by IV. Even assuming a placebo effect, the mean change from baseline for the ETT seconds still allowed an unexpectedly favorable comparison of results with angioplasty.

When the quality of life of 48 human CAD patients was assessed by a validated, disease specific questionnaire, the Seattle Angina Questionnaire (SAQ), at baseline (i.e., prior to dosing), and at 2 and 6 months after a single receiving a single unit dose of rFGF-2 of the present invention by IC or IV routes, the mean change from baseline for the 5 scales measured by the SAQ increased in a clinically significant manner for all dosage ranges whether administered IC or IV (Tables 2-6). In particular, the five scales assessed by the SAQ are exertional capacity, angina stability, angina frequency, treatment satisfaction, and disease perception. Relative to the baseline, the mean score for exertional capacity increased by 10.9 to 20.2 at 2 months; and by 16.5 to 24.1 at 6 months. For angina stability, the mean score increased by 32.1 to 46.2 at 2 months; and by 16.7 to 23.2 at 6 months. For angina frequency, the mean score increased by 20.0 to 32.9 at 2 months; and by 11.4 to 36.7 at 6 months. For treatment satisfaction, the mean score increased by 8.5 to 19.8 at 2 months; and by 6.3 to 19.8 at 6 months. For disease perception, the mean score increased by 20.2 to 27.8 at 2 months; and by 23.8 to 34.0 at 6 months. Generally, a change of 8 points on any scale is considered clinically significant. Thus, the observed changes of 8.5-46.2 are clinically significant for each of the five scales that were assessed. Even assuming a placebo effect whereby a mean change from baseline of 14 points is considered clinically significant, the results still provide for an unexpectedly superior effect at almost all scales that were assessed.

As part of this study, MRI was also performed on 33 human patients diagnosed with CAD to assess the effect of administering a single unit dose of rFGF-2 on their cardiac ejection fraction, regional myocardial function and perfusion (delayed arrival zone). Specifically, the patients were administered a single unit dose of 0.33 µg/kg to 48 µg/kg IC or 18 µg/kg to 36 µg/kg IV of rFGF-2 of SEQ ID NO:2. When the 33 human CAD patients were assessed by resting cardiac magnetic resonance imaging (MRI) at baseline (i.e., prior to treatment), and 1, 2 and 6 months after treatment with a single unit dose of rFGF-2 of the invention by IC or IV routes, the patients exhibited a highly statistically significant response to the method of treatment as objectively measured by increased target wall thickening, target wall motion, and target area collateral extent, and by decreased target area delayed arrival extent. By way of summary, at 1, 2 and 6 months, the target wall thickening increased relative to baseline at 4.4%, 6.3% and 7.7%, respectively; the target wall motion increased relative to baseline at 2.7%, 4.4% and 6.4%, respectively; the target area collateral extent increased relative to baseline at 8.3%, 10.9% and 11.2%, respectively; and the target area delayed arrival extent decreased relative to baseline at −10.0%, −8.3% and −10.0%, respectively.

The above data demonstrates the clinical efficacy in humans of the present unit dose composition of rFGF-2 or an angiogenically active fragment thereof when administered IC or IV in accordance with the present invention.

BRIEF DESCRIPTION OF THE FIGURES

FIG. 2 is a plot of mean FGF-2 area under the curve (AUC) in pg*min/ml corresponding to FIGS. 1A and 1B. This plot shows the dose linearity of systemic rFGF-2 exposure following IC or IV infusion. The systemic exposure for the IC route is similar to that observed following IV administration.

FIG. 3 is a plot of individual human patient FGF-2 plasma clearance (CL) values as a function of the time of heparin administration in "minutes prior to rFGF-2 infusion" and shows the influence of timing of heparin administration on rFGF-2 plasma clearance (CL).

DETAILED DESCRIPTION OF THE INVENTION

Figure 1A:
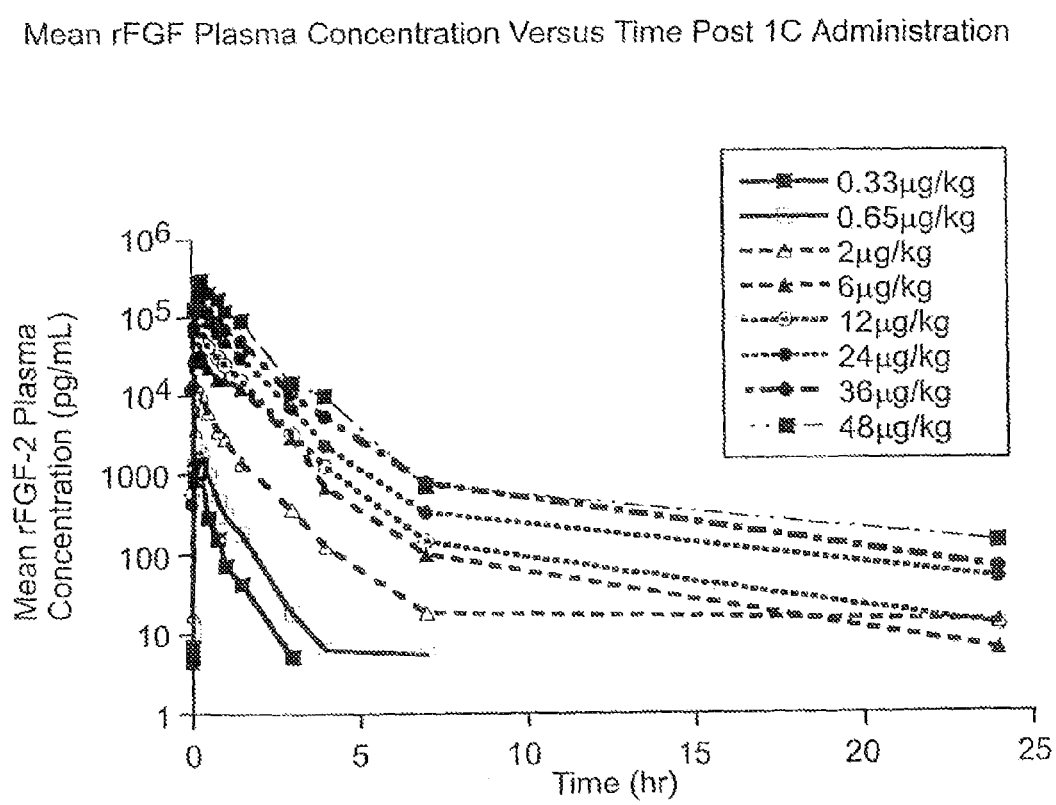
FIG. 1A is a plot of the mean rFGF-2 plasma concentration versus time profiles for eight different doses of rFGF-2 (SEQ ID NO:2) administered by IC infusion in humans over a 20 minute period. The eight doses of rFGF-2 presented in FIG. 1A are 0.33, 0.65, 2, 6, 12, 24, 36, and 48 µg/kg of lean body mass (LBM).

The Applicants have discovered that a single dose of rFGF-2 or an angiogenically active fragment or mutein thereof, when administered in a safe and therapeutically effective amount into one or more coronary vessels or into a peripheral vein of a human patient diagnosed with CAD provides the patient with a safe and therapeutically efficacious treatment for the patient's coronary artery disease that lasts at least 4 to 6 months, more typically at least six months, before a further treatment is needed. This duration of the effect and the magnitude of the improvements in ETT, SAQ and MRI were unexpected for a single unit dose of medicament.

By the phrase "therapeutically effective amount" or "safe and therapeutically effective amount" as used herein in relation to rFGF-2 is meant an amount of rFGF-2 or an angiogenically active fragment or mutein thereof that when administered in accordance with this invention, is free from major complications that cannot be medically managed, and that provides for objective cardiac improvement in patients having symptoms of CAD despite optimum medical management. Thus, acute hypotension that can be managed by administration of fluids, is considered "safe" for the purpose of this invention. Typically, the safe and therapeutically effective amount of rFGF-2 comprises about 0.2 µg/kg to about 48 µg/kg of rFGF-2 or an angiogenically active fragment or mutein thereof. A suitable FGF-2 for use in the present invention is the rFGF-2 of SEQ ID NO:2 or an angiogenically active fragment or mutein thereof.

Accordingly, the present invention has multiple aspects. In its first aspect, the present invention is directed to a unit dose composition for inducing angiogenesis in a human patient, the unit dose comprising a therapeutically effective (i.e., an angiogenically effective) amount of rFGF-2 or an angiogenically active fragment or mutein thereof, the amount comprising about 0.2 µg/kg to about 48 µg/kg of rFGF-2 or an angiogenically active fragment or mutein thereof.

By the term "unit dose composition" as used herein is meant a composition that when administered to a human patient in accordance with the method of the present invention provides a typical human patient in need of angiogenesis with an angiogenic effect of significant efficacy so as not to require retreatment for at least 4-6 months, typically 6 months. The unit dose composition of the present invention is typically provided in combination with one or more pharmaceutically acceptable excipients or carriers. In other embodiments of the unit dose composition, a safe and therapeutically effective amount comprises about 0.2 µg/kg to about 2 µg/kg, about 2 µg/kg to about 24 µg/kg, or about 24 µg/kg to about 48 µg/kg of rFGF-2 or an angiogenically active fragment or mutein thereof.

It is convenient to define the unit dose composition of the present invention in more absolute terms that are not dependent upon the weight of the patient to be treated. When so defined, the unit dose composition comprises from 0.008 mg to 7.2 mg of rFGF-2 or an angiogenically active fragment or mutein thereof. In this embodiment, the unit dose composition contains a sufficient amount of FGF-2 to accommodate dosing any one of the majority of human CAD patients, ranging from the smallest patient (e.g., 40 kg) at the lowest dosage (about 0.2 µg/kg) through the larger patients (e.g., 150 kg) at the highest dosage (about 48 µg/kg). More typically, the unit dose comprises 0.3 mg to 3.5 mg of rFGF-2 or an angiogenically active fragment or mutein thereof. The unit dose composition is typically provided in solution or lyophilized form containing the above referenced amount of rFGF-2 and an effective amount of one or more pharmaceutically acceptable buffers, stabilizers and/or other excipients as later described herein.

The active agent in the Applicants' above described unit dose composition is a recombinant FGF-2 or an angiogenically active fragment or mutein thereof. Methods for making recombinant FGF-2 are well-known in the art. The recombinant FGF-2 of SEQ ID NO:2 is made as described in U.S. Pat. No. 5,155,214, entitled "Basic Fibroblast Growth Factor," which issued on Oct. 13, 1992, and which is expressly incorporated herein by reference in its entirety. Moreover, all other references cited herein, whether occurring before or after this sentence, are expressly incorporated herein by reference in their entirety. As disclosed in the '214 patent, a DNA of SEQ ID NO:1, which encodes a bFGF (hereinafter "FGF-2") of SEQ ID NO:2, is inserted into a cloning vector, such as pBR322, pMB9, Col E1, pCR1, RP4 or λ-phage, and the cloning vector is used to transform either a eukaryotic or prokaryotic cell, wherein the transformed cell expresses the FGF-2. In one embodiment, the host cell is a yeast cell, such as *Saccharomyces cerevisiae*. The resulting full length FGF-2 that is expressed has 146 amino acids in accordance with SEQ ID NO:2. Although the FGF-2 of SEQ ID NO:2 has four cysteines, i.e., at residue positions 25, 69, 87 and 92, there are no internal disulfide linkages. ['214 at col. 6, lines 59-61.] However, in the event that cross-linking occurred under oxidative conditions, it would likely occur between the residues at positions 25 and 69.

The FGF-2 of SEQ ID NO:2, which has 146 amino acid residues, differs from naturally occurring human FGF-2 by only two amino acid residue. In particular, the amino acids at residue positions 112 and 128 of the FGF-2 of SEQ ID NO:2 are Ser and Pro, respectively, whereas in human FGF-2, they are Thr and Ser, respectively. In nature, bovine FGF-2, like the corresponding human FGF-2 is initially synthesized in vivo as a polypeptide having 155 amino acid residues. Abraham et al. "*Human Basic Fibroblast Growth Factor: Nucleotide Sequence and Genomic Organization,*" EMBO J., 5(10):2523-2528 (1986). When the FGF-2 of SEQ ID NO:2 is compared to the full length 155 residue bovine FGF-2 of Abraham, the FGF-2 of SEQ ID NO:2 lacks the first nine amino acid residues, Met Ala Ala Gly Ser Ile Thr Thr Leu (SEQ ID NO:3), at the N-terminus of the corresponding full length molecule. The recombinant FGF-2 employed in the present compositions and method was purified to pharmaceutical quality (98% or greater purity) using the techniques described in detail in U.S. Pat. No. 4,956,455, entitled "Bovine Fibroblast Growth Factor" which issued on Sep. 11, 1990 and which is incorporated herein by reference in its entirety. In particular, the first two steps employed in the purification of the recombinant FGF-2 of Applicants' unit dose composition are "conventional ion-exchange and reverse phase HPLC purification steps as described previously." [U.S. Pat. No. 4,956,455, citing to Bolen et al., PNAS USA 81:5364-5368 (1984).] The third step, which the '455 patent refers to as the "key purification step" ['455 at col. 7, lines 5-6], is heparin-SEPHAROSE® affinity chromatography, wherein the strong heparin binding affinity of the FGF-2 is utilized to achieve several thousand-fold purification when eluting at approximately 1.4M and 1.95M NaCl ['455 at col. 9, lines 20-25]. Polypeptide homogeneity was confirmed by reverse-phase high pressure liquid chromatography (RP-HPLC). Buffer exchange was achieved by SEPHADEX® G-25(M) gel filtration chromatography.

In addition to the 146 residue rFGF-2 of SEQ ID NO:2, the active agent in the unit dose of the present invention also comprises an "angiogenically active fragment" of FGF-2. By the term "angiogenically active fragment" of FGF-2 is meant a fragment of FGF-2 that has about 80% of the 146 residues of SEQ ID NO:2 and that retains at least 50%, preferably at least 80%, of the angiogenic activity of the FGF-2 of SEQ ID NO:2.

To be angiogenically active, the FGF-2 fragment should have two cell binding sites and at least one of the two heparin binding sites. The two putative cell binding sites of the analogous human FGF-2 occur at residue positions 36-39 and 77-81 thereof. See Yoshida, et al., "*Genomic Sequence of hst, a Transforming Gene Encoding a Protein Homologous to Fibroblast Growth Factors and the int-2-Encoded Protein,*" PNAS USA, 84:7305-7309 (October 1987) at FIG. 3. The two putative heparin binding sites of hFGF-2 occur at residue positions 18-22 and 107-111 thereof. See Yoshida (1987) at FIG. 3. Given the greater than 98% similarity between the amino acid sequences for naturally occurring human FGF-2 (hFGF-2) and rFGF-2 (SEQ ID NO:2), it is expected that the two cell binding sites for rFGF-2 (SEQ ID NO:2) are also at residue positions 36-39 and 77-81 thereof, and that the two heparin binding sites are at residue positions 18-22 and 107-111 thereof. Consistent with the above, it is well known in the art that N-terminal truncations of the FGF-2 of SEQ ID NO:2 do not eliminate its activity in cows. In particular, the art discloses several naturally occurring and biologically active fragments of the FGF-2 that have N-terminal truncations relative to the FGF-2 of SEQ ID NO:2. An active and truncated bFGF-2 having residues 12-146 of SEQ ID NO:2 was found in bovine liver and another active and truncated bFGF-2, having residues 16-146 of SEQ ID NO:2 was found in the bovine kidney, adrenal glands and testes. [See U.S. Pat. No. 5,155,214 at col. 6, lines 41-46, citing to Ueno, et al., Biochem and Biophys Res. Comm., 138:580-588 (1986).] Likewise, other fragments of the bFGF-2 of SEQ ID NO:2 that are known to have FGF activity are FGF-2 (24-120)-OH and FGF-2 (30-110)-NH$_2$. [U.S. Pat. No. 5,155,214 at col. 6, lines 48-52.] These latter fragments retain both of the cell binding portions of FGF-2 (SEQ ID NO:2) and one of the heparin binding segments (residues 107-111). Accordingly, the angiogenically active fragments of FGF-2 typically encompass those terminally truncated fragments of FGF-2 that have at least residues that correspond to residues 30-110 of FGF-2 of SEQ ID NO:2; more typically, at least residues that correspond to residues 18-146 of FGF-2 of SEQ ID NO:2.

The unit dose of the present invention also comprises an "angiogenically active . . . mutein" of the rFGF-2 of SEQ ID NO:2. By the term "angiogenically active . . . mutein" as used herein, is meant an isolated and purified recombinant protein or polypeptide that has 65% sequence identity (homology) to any naturally occurring FGF-2, as determined by the Smith-Waterman homology search algorithm (*Meth. Mol. Biol.* 70:173-187 (1997)) as implemented in MSPRCH program (Oxford Molecular) using an affine gap search with the following search parameters: gap open penalty of 12, and gap extension penalty of 1, and that retains at least 50%, preferably at least 80%, of the angiogenic activity of the naturally occurring FGF-2 with which it has said at least 65% sequence identity. Preferably, the angiogenically active mutein has at least 75%, more preferably at least 85%, and most preferably, at least 90% sequence identity to the naturally occurring FGF-2. Other well-known and routinely used homology/identity scanning algorithm programs include Pearson and Lipman, *PNAS USA,* 85:2444-2448 (1988); Lipman and Pearson, *Science,* 222:1435 (1985); Devereaux et al., *Nuc. Acids Res.,* 12:387-395 (1984); or the BLASTP, BLASTN or BLASTX algorithms of Altschul, et al., *Mol. Biol.,* 215:403-410 (1990). Computerized programs using these algorithms are also available and include, but are not limited to: GAP, BESTFIT, BLAST, FASTA and TFASTA, which are commercially available from the Genetics Computing Group (GCG) package, Version 8, Madison Wis., USA; and CLUSTAL in the PC/Gene program by Intellegenetics, Mountain View Calif. Preferably, the percentage of sequence identity is determined by using the default parameters determined by the program.

The phrase "sequence identity," as used herein, is intended to refer to the percentage of the same amino acids that are found similarly positioned within the mutein sequence when a specified, contiguous segment of the amino acid sequence of the mutein is aligned and compared to the amino acid sequence of the naturally occurring FGF-2.

When considering the percentage of amino acid sequence identity in the mutein, some amino acid residue positions may differ from the reference protein as a result of conservative amino acid substitutions, which do not affect the properties of the protein or protein function. In these instances, the percentage of sequence identity may be adjusted upwards to account for the similarity in conservatively substituted amino acids. Such adjustments are well-known in the art. See, e.g., Meyers and Miller, "*Computer Applic. Bio. Sci.,* 4:11-17 (1988).

To prepare an "angiogenically active mutein" of an angiogenic agent of the present invention, one uses standard techniques for site directed mutagenesis, as known in the art and/or as taught in Gilman, et al., *Gene,* 8:81 (1979) or Roberts, et al., *Nature,* 328:731 (1987). Using one of the site directed mutagenesis techniques, one or more point mutations are introduced into the cDNA sequence of SEQ ID NO: 1 to introduce one or more amino acid substitutions or an internal deletion. Conservative amino acid substitutions are those that preserve the general charge, hydrophobicity/hydrophilicity, and/or steric bulk of the amino acid being substituted. By way of example, substitutions between the following groups are conservative: Gly/Ala, Val/Ile/Leu, Lys/Arg, Asn/Gln, Glu/Asp, Ser/Cys/Thr, and Phe/Trp/Tyr. Significant (up to 35%) variation from the sequence of the naturally occurring angiogenic FGF-2 is permitted as long as the resulting protein or polypeptide retains angiogenic activity within the limits specified above.

Cysteine-depleted muteins are muteins within the scope of the present invention. These muteins are constructed using site directed mutagenesis as described above, or according to the method described in U.S. Pat. No. 4,959,314 ("the '314 patent"), entitled "Cysteine-Depleted Muteins of Biologically Active Proteins." The '314 patent discloses how to determine biological activity and the effect of the substitution. Cysteine substitution is particularly useful in proteins having two or more cysteines that are not involved in disulfide formation. Suitable substitutions include the substitution of serine for one or both of the cysteines at residue positions 87 and 92, which are not involved in disulfide formation. Preferably, substitutions are introduced at the FGF-2 N-terminus, which is not associated with angiogenic activity. However, as discussed above, conservative substitutions are suitable for introduction throughout the molecule.

The unit dose composition of the present invention comprises a safe and an angiogenically effective dose of rFGF-2 or an angiogenically active fragment or mutein thereof, and a pharmaceutically acceptable carrier. Typically, the safe and angiogenically effective dose of the pharmaceutical composition of the present invention is in a form and a size suitable for administration to a human patient and comprises (i) 0.2 µg/kg to 48 µg/kg of rFGF-2 or an angiogenically active fragment or mutein thereof, (ii) and a pharmaceutically acceptable carrier. In other embodiments, the safe and angiogenically effective dose comprises 0.2 µg/kg to 2 µg/kg, >2 µg/kg to <24 µg/kg or 24 µg/kg to 48 µg/kg of FGF-2 or an angiogenically active fragment or mutein thereof, and a pharmaceutically acceptable carrier. Expressed in absolute terms for the majority of human CAD patients, the unit dose of the present invention comprises 0.008 mg to 7.2 mg, more typically 0.3 mg to 3.5 mg, of the FGF-2 or an angiogenically active fragment or mutein thereof.

The second recited component of the unit dose composition of the present invention is a "pharmaceutically acceptable carrier." By the term "pharmaceutically acceptable carrier" as used herein is meant any of the carriers or diluents that are well-known in the art for the stabilization and/or administration of a proteinaceous medicament that does not itself induce the production of antibodies harmful to the patient receiving the composition, and which may be administered without undue toxicity. The choice of the pharmaceutically acceptable carrier and its subsequent processing enables the unit dose composition of the present invention to be provided in either liquid or solid form.

When the unit dose composition is in liquid form, the pharmaceutically acceptable carrier comprises a stable carrier or diluent suitable for intravenous ("IV") or intracoronary ("IC") injection or infusion. Suitable carriers or diluents for injectable or infusible solutions are nontoxic to a human recipient at the dosages and concentrations employed, and include sterile water, sugar solutions, saline solutions, protein solutions or combinations thereof.

Typically, the pharmaceutically acceptable carrier includes a buffer and one or more stabilizers, reducing agents, antioxidants and/or anti-oxidant chelating agents. The use of buffers, stabilizers, reducing agents, anti-oxidants and chelating agents in the preparation of protein based compositions, particularly pharmaceutical compositions, is well-known in the art. See, Wang et al., "*Review of Excipients and pHs for Parenteral Products Used in the United States,*" *J. Parent. Drug Assn.,* 34(6):452-462 (1980); Wang et al., "*Parenteral Formulations of Proteins and Peptides: Stability and Stabilizers,*" *J. Parent. Sci. and Tech.,* 42:S4-S26 (Supplement 1988); Lachman, et al., "*Antioxidants and Chelating Agents as Stabilizers in Liquid Dosage Forms-Part 1,*" *Drug and Cosmetic Industry,* 102(1): 36-38, 40 and 146-148 (1968); Akers, M. J., "*Antioxidants in Pharmaceutical Products,*" *J. Parent. Sci. and Tech.,* 36(5):222-228 (1988); and Methods in Enzymology, Vol. XXV, Colowick and Kaplan Eds., "*Reduction of Disulfide Bonds in Proteins with Dithiothreitol,*" by Konigsberg, pages 185-188. Suitable buffers include acetate, adipate, benzoate, citrate, lactate, maleate, phosphate, tartarate and the salts of various amino acids. See Wang (1980) at page 455. Suitable stabilizers include carbohydrates such as threlose or glycerol. Suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2-3); and thioglycerol at 0.1% to 0.5% (pH 3.5 to 7.0) and glutathione. See Akers (1988) at pages 225 to 226. Suitable antioxidants include sodium bisulfite, sodium sulfite, sodium metabisulfite, sodium thiosulfate, sodium formaldehyde sulfoxylate, and ascorbic acid. See Akers (1988) at pages 225. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See e.g., Wang (1980) at pages 457-458 and 460-461, and Akers (1988) at pages 224-227. Suitable sugars include glycerol, trehalose, glucose, galactose and mannitol, sorbitol. A suitable protein is human serum albumin.

In liquid form, a typical unit dose composition of the present invention comprises from about 0.001 mg to 8 mg, more typically 0.03 to 5 mg rFGF-2 or an angiogenically active fragment or mutein thereof, dissolved a pharmaceutically acceptable carrier. A suitable pharmaceutically acceptable carrier comprises 10 mM thioglycerol, 135 mM NaCl, 10 mM sodium citrate, and 1 mM EDTA, pH 5. A suitable diluent or flushing agent for the above-described unit dose composition is any of the above-described carriers. Typically, the diluent is the carrier solution. rFGF-2 or an angiogenically active fragment or mutein thereof is unstable for long periods of time in liquid form. To maximize stability and shelf life of the liquid form, the unit dose composition should be stored frozen at −60° C. When thawed, the solution is stable for 6 months at refrigerated conditions. A typical unit dose would comprise about 1-40 ml, more typically 10-40 ml, of the above-described composition having 0.008-7.2 mg of rFGF-2 or an angiogenically active fragment or mutein dissolved therein. A suitable rFGF-2 for use in the unit dose is the rFGF-2 of SEQ ID NO:2 or an angiogenically active fragment or mutein thereof.

In another embodiment, the unit dose composition is provided in lyophilized (freeze-dried) form. In this form, the unit dose of rFGF-2 is capable of being stored at refrigerated temperatures for substantially longer than 6 months without loss of therapeutic effectiveness. Lyophilization is accomplished by the rapid freeze drying (i.e., removing water) under reduced pressure of a plurality of vials, each containing the above described liquid form of the unit dose of the rFGF-2 of the present invention therein. Lyophilizers, which perform the above described lyophilization, are commercially available and readily operable by those skilled in the art. The resulting lyophilized unit dose composition, in lyophilized cake form, is formulated to contain within the resulting lyophilized cake one or more of the buffers, stabilizers, anti-oxidants, reducing agents, salts and/or sugars described above for the corresponding liquid formulation. A lyophilized unit dose composition containing all such other components need only be reconstituted to a known volume or concentration with sterile aqueous diluent such as sterile water, a sterile sugar solution, or a sterile saline solution. Alternatively, it could be reconstituted with a sterile buffer solution as described above, but lacking a chelating agent, such as EDTA. As a lyophilized cake, the unit dose composition is stable from 6 months to two years at refrigerated temperatures. Thus, storage of the unit dose composition in lyophilized form is readily accommodated using conventional refrigeration equipment.

Because the unit dose composition of the present invention is administered via a cardiac catheter or other injection device, which has dead space, it is convenient to formulate the vial containing the unit dose composition so that it contains about 10-50% more of the rFGF-2 or angiogenically active fragment or mutein thereof than is to be administered to the patient. For example, when the unit dose of the rFGF-2 to be administered is 7.2 mg, the vial is optionally formulated to contain up to 50% extra (e.g., a total of about 10.8 mg) of rFGF-2 or angiogenically active fragment or mutein thereof. The extra solution is suitable for filling the dead space in the delivery equipment. In an alternative embodiment that does not allow for dead space, the pharmaceutical composition is loaded in the cardiac catheter in front of a pharmaceutically acceptable buffer, diluent or carrier, which is then used to deliver the appropriate amount of the one or more dosages to the one or more sites in the myocardium that are in need of angiogenesis.

As discussed above, the pharmaceutically acceptable carrier for the above described unit dose composition comprises a buffer and one or more stabilizers, reducing agents, anti-oxidants and/or anti-oxidant chelating agents. It is also within the scope of the present invention that the unit dose composition contain an amount of a glycosoaminoglycan (also known as a "proteoglycan" or a "mucopolysaccharide"), such as heparin, that is effective to bind to the FGF-2 and to the endothelial cell receptors so as to enhance the angiogenic effectiveness of the FGF-2 or angiogenically active fragment or mutein thereof. The amount of heparin that is administered is about 10-80 U per kg of patient weight (U/kg), typically about 40 U/kg. Expressed in absolute terms, the total amount of heparin administered to any one patient does not exceed 5,000 U. Thus, upon reconstitution, the unit dose composition of the present invention would not only contain an angiogenically effective amount of rFGF-2 or an angiogenically active fragment or mutein thereof, it would also contain from about 10-80 U/kg of heparin, typically about 40 U/kg. The typical volume of diluent is from about 1 to 40 ml. While larger volumes of diluent could be used, such larger volumes would typically result in longer administration times. Depending upon the weight of the patient in kg, a single dose comprising from 0.2 µg/kg to 48 µg/kg of the rFGF-2 or an angiogenically active fragment or mutein thereof is withdrawn from the vial as reconstituted product for administration to the patient. Thus, an average 70 kg man that is being dosed at 24 µg/kg would have a sufficient volume of the reconstituted product withdrawn from the vial to receive an IC infusion of (70 kg×30 µg/kg) 2100 µg (i.e., 2.1 mg).

In its second aspect, the present invention is directed to a method for treating a human patient for CAD or MI, using the above described unit dose composition. In particular, in one embodiment, the present invention is directed to a method for treating a human patient for coronary artery disease, comprising administering a safe and therapeutically effective amount of a recombinant FGF-2 or an angiogenically active fragment or mutein thereof to one or more, typically two, patient coronary vessels or a peripheral vein of a human patient in need of treatment for coronary artery disease. The human patient in need of treatment for coronary artery disease is typically a human patient with coronary artery disease who remains symptomatic with angina despite optional medical management. A preferred coronary vessel is a coronary artery, although grafted saphenous veins and grafted internal mammary arteries, as provided by coronary angioplasty, are also suitable. Suitable peripheral veins for administering the unit dose composition include those peripheral veins found throughout the human body that are routinely used by treating physicians and nurses for administration of fluids and medicaments. Examples of such veins include the cephalic, the median cubital, and the basilic of the arm.

When administered as an intracoronary (IC) infusion, the unit dose of rFGF-2 or angiogenic fragment or mutein thereof is typically administered within an hour, more typically over a period of about 20 minutes into one or more (typically, two) patient coronary vessels. When administered over a twenty minute period, the unit dose composition is typically administered at a rate of 0.5 to 2.0 ml/minute, more typically at about 1 ml/minute. The coronary vessels can be native vessels or grafts, so long as they are not occluded. The volume of the unit dose of rFGF-2 or angiogenic fragment or mutein thereof is typically 10-40 ml; more typically 20 ml. The length of time for infusion of the unit dose is not critical and can be shortened or lengthened depending on the rate and volume of infusion.

When administered as an intravenous (IV) infusion, the unit dose of rFGF-2 or angiogenic fragment or mutein thereof is administered typically within an hour, more typically over a 20 minute period, into a peripheral vein using a conventional IV setup. When administered over a twenty minute period, the unit dose composition is typically administered at a rate of 1 ml/minute.

In the phase I clinical trial of the above described method for treating CAD, a single unit dose composition was administered IC or IV to human patients having CAD who remained symptomatic with angina despite optional medical management. Because the method of the present invention induces angiogenesis, the method of the present invention provides treatment of the underlying condition in CAD or MI and not merely transitory relief from the symptoms, such as provided by nitrates. Typically, the safe and therapeutically effective amount of the method of the present invention comprises 0.2 µg/kg to 48 µg/kg of rFGF-2 or an angiogenically active fragment or mutein thereof in a pharmaceutically acceptable carrier. In other embodiments, the safe and therapeutically effective amount comprises 0.2 µg/kg to 2 µg/kg, >2 µg/kg to <24 µg/kg, or 24 µg/kg to 48 µg/kg of rFGF-2 or an angiogenically active fragment or mutein thereof in a pharmaceutically acceptable carrier. In absolute terms, the safe and therapeutically effective amount is about 0.008 mg to about 7.2 mg of rFGF-2 or an angiogenically active fragment or mutein thereof; more typically, 0.3 mg to 3.5 mg of rFGF-2 or an angiogenically active fragment or mutein thereof. A suitable rFGF-2 is the rFGF-2 of SEQ ID NO:2 or an angiogenically active fragment or mutein thereof.

In another aspect, the present invention is also directed to a method for inducing angiogenesis in a heart of a human patient comprising, administering a single unit dose composition of a recombinant FGF-2 or an angiogenically active fragment or mutein thereof to one or more coronary vessels or to a peripheral vein in a human patient in need of coronary angiogenesis, said unit dose composition comprising from about 0.008 mg to 7.2 mg of recombinant rFGF-2 or an angiogenically active fragment or mutein thereof in a pharmaceutically acceptable carrier. More typically, the unit dose composition comprises about 0.3-3.5 mg rFGF-2 or an angiogenically active fragment or mutein thereof in a pharmaceutically acceptable carrier. As described above, a single unit dose composition containing a therapeutically effective amount of an rFGF-2 or an angiogenically fragment or mutein thereof is administered to at least one coronary vessel of a human patient in need of angiogenesis, using standard cardiac catheterization techniques already known and used in the art for the intracoronary administration of medicaments, e.g., thrombolytics, streptokinase, or radio-opaque dyes or magnetic particles used to visualize the coronary arteries. By way of example, a coronary catheter is inserted into an artery (e.g., femoral or subclavian) of the patient in need of treatment and the catheter is pushed forward, with visualization, until it is positioned in the appropriate coronary vessel of the patient to be treated. Using standard precautions for maintaining a clear line, the pharmaceutical composition in solution form is administered by infusing the unit dose substantially continuously over a period of 10 to 30 minutes. Although the pharmaceutical composition of the invention could be administered over a longer period of time, the Applicants perceive no benefit and a potentially increased risk of thrombosis in doing so. Typically, a portion (e.g., one half) of the unit dose is administered in a first coronary vessel. Then, the catheter is repositioned into a second secondary coronary vessel and the remainder of the unit dose is administered with flushing of the catheter. Using the above-described repositioning procedure, portions of the unit dose may be administered to a plurality of coronary vessels until the entire unit dose has been administered. After administration, the catheter is withdrawn using conventional art known protocols. In the phase I clinical trials described herein, therapeutic benefit was reported by patients as early as two weeks following the IC rFGF-2 administration of a single unit dose. Clinically significant improvement was demonstrable by objective criterion (ETT and/or SAQ) as early as 30 days following IC or IV administration of a single unit dose of the present invention, and was maintained for six months following dosing. In certain patients with progressive CAD disease, it may be necessary or appropriate to administer additional unit doses of rFGF-2 at six or 12 month intervals after the initial unit dose, to overcome the progression of the CAD during that interim period. In some patients with very progressive CAD, unit doses of present invention would be readministered at 4 month intervals. In any instance, the treating physician would be able to determine the time, if any, for readministration based upon routine assessment of the clinical symptoms of the patient.

One of the benefits of the method of the present invention is cardiac angiogenesis. Accordingly, in another aspect, the present invention is directed to a method for inducing angiogenesis in a heart of a human patient, comprising administering into one or more coronary vessels (IC) or into a peripheral vein (IV) of a human patient in need of coronary angiogenesis, a single unit dose composition comprising an angiogenically effective amount of rFGF-2 or an angiogenically active fragment or mutein thereof in a pharmaceutically acceptable carrier. In the above method, the angiogenically effective amount comprises about 0.2 µg/kg to about 48 µg/kg (or in absolute terms about 0.008 mg to about 7.2 mg) of a recombinant FGF-2 or an angiogenically active fragment or mutein thereof. More typically, the angiogenically effective amount comprises about 0.3 mg to 3.5 mg of a recombinant FGF-2 or an angiogenically active fragment or mutein thereof. A suitable rFGF-2 for use in the above-identified method is the rFGF-2 of SEQ ID NO:2 or an angiogenically active fragment thereof. In one embodiment of the above method, the unit dose composition is administered IC to patient coronary vessels or IV to a peripheral vein. In another embodiment, the unit dose composition is administered with heparin as described herein.

The above described method for providing coronary angiogenesis is also beneficial in human patients that have undergone a myocardial infarction (MI) in one or more coronary arteries. Accordingly, in another aspect, the present invention is also directed to a method for treating a human patient for an MI comprising, administering into one or more coronary vessels or into a peripheral vein of said human patient, a single unit dose composition comprising a therapeutically effective amount of rFGF-2 or an angiogenically active fragment or mutein thereof. In the above method, the unit dose composition typically comprises about 0.2 µg/kg to about 48 µg/kg (or in absolute terms about 0.008 mg to about 7.2 mg) of a recombinant FGF-2 or an angiogenically active fragment or mutein thereof in a pharmaceutically acceptable carrier. A suitable rFGF-2 for use in the above-identified method is the rFGF-2 of SEQ ID NO:2 or an angiogenically active fragment thereof.

In the event of unstable angina or acute myocardial infarction, requiring angioplasty, the same doses of rFGF-2 or angiogenic fragment or mutein thereof that are disclosed herein would also be useful as an adjunct therapy in treating those conditions. Accordingly, in another aspect, the present invention is directed to an improved method for treating a patient for unstable angina or acute myocardial infarction, requiring angioplasty, the method comprising providing angioplasty to the patient in need of treatment; the improvement comprising administering into one or more coronary vessels or into a peripheral vein of said human patient, a single unit dose composition comprising a therapeutically effective amount of rFGF-2 or an angiogenically active fragment or mutein thereof. In the above method, the unit dose composition comprises about 0.2 µg/kg to about 48 µg/kg (or in absolute terms about 0.008 mg to about 7.2 mg) of a recombinant FGF-2 or an angiogenically active fragment or mutein thereof in a pharmaceutically acceptable carrier. A suitable rFGF-2 for use in the above-identified method is the rFGF-2 of SEQ ID NO:2 or an angiogenically active fragment thereof.

In any of the above-described methods of the present invention, the rFGF-2 or the angiogenically active fragment or mutein thereof is associated with release of nitric oxide, a recognized smooth muscle dilator, which upon administration to the patient causes a sudden drop in the patient's blood pressure. Accordingly, in the methods of the present invention, it is preferable to hydrate the patient with IV fluids prior to administering the unit dose of the present invention. Moreover, for safety and tolerability of the unit dose, aggressive fluid management during and after rFGF-2 administration is also preferred. Finally, it is also within the scope of the above described methods to include the step of administering an effective amount of a glycosoaminoglycan (also known as a "proteoglycan" or a "mucopolysaccharide"), such as heparin from 0-30 minutes prior to administering the unit dose composition of the present invention. Typically, the effective amount of glycosaminoglycan (such as heparin) that is administered is about 10-80 U/kg, more typically, about 40 U/kg. However, the total amount of heparin administered to any one patient immediately prior to dosing generally does not exceed 5,000 U.

Because EDTA is a potent chelator of calcium which is required for normal myocardial contraction and cardiac conduction, minimizing the concentration of EDTA is critical to patient's safety. A concentration of EDTA less than 100 μg/ml optimized the safety of administration of rFGF-2 by IC or IV infusion to human patients.

Because a sudden bolus of rFGF-2 is associated with profound hypotension in animals, the rate of infusion is critical to patient's safety. Administration at 0.5 to 2 mL per minute, typically 1 mL per minute, optimized the safety of administration of rFGF-2 by IC or IV infusion to human patients.

A Phase I clinical trial directed to treating human patients for CAD by administering a single unit dose composition of the present invention was conducted and is described in Examples 1-3 herein. In that trial, sixty-six (66) human patients diagnosed with CAD, who satisfied the criteria of Example 2 herein, received a single unit dose of rFGF-2 in accordance with the method of the present invention. Specifically, fifty-two human patients were administered a unit dose of 0.33 μg/kg to 48 μg/kg of rFGF-2 by IC infusion over about a 20 minute period. Fourteen human patients were administered a unit dose of either 18 μg/kg or 36 μg/kg of rFGF-2 by IV infusion over about a 20 minute period. The 66 treated patients were then assessed relative to baseline (i.e., prior to treatment with the single unit dose), and again at 1 month, 2 months and 6 months after treatment with the single unit dose, using three sets of art-recognized assessment criteria: 1) changes in their exercise tolerance time (ETT); 2) the Seattle Angina Questionnaire, which provides an assessment based upon a mixed combination of objective and subjective criteria; and 3) the measurement of physical changes in the heart as assessed by MRI.

For ETT of the 66 patients of the Phase I clinical trial of Examples 1-3 was measured at baseline, and at 1 month, 2 months and 6 months after dosing (with a single unit dose composition of the invention) using a Bruce treadmill protocol. Subjects were excluded from the analysis if the treadmill protocol was not the same as used at baseline. Therefore, the number of subjects varied over time. In addition, any patients who had emergency revascularization were excluded from the analysis. A dose was considered effective if the mean change in ETT from baseline increased by greater than 60 seconds. The results of the ETT assessment are provided in Table 1.

TABLE 1

Exercise Tolerance Time (ETT) - Change from Baseline

| FGF-2 Dose Group | Change from Baseline at One Month | Change from Baseline at Two Months | Change from Baseline at Six Months |
| --- | --- | --- | --- |
| 0.33 to 2.0 μg/kg IC | N = 8 | N = 6 | N = 5 |
| (N = 16) | 45.1 sec | 130.0 sec* | 60.8 sec |
| (low) | (−105 to 180) | (19 to 240) | (−45 to 210) |
| 6.0 and 12 μg/kg IC | N = 2 | N = 4 | N = 2 |
| (N = 8) | −24.0 sec | −2.5 sec | 6.5 sec |
| (mid) | (−48 to 0) | (−90 to 120) | (−0 to 13) |
| 24.0 to 48.0 μg/kg IC | N = 18 | N = 21 | N = 16 |
| (N = 28) | 51.9 sec | 107.9 sec* | 133.1 sec* |
| (high) | (−188 to 399) | (−30 to 385) | (−195 to 386) |
| 18.0 & 36.0 μg/kg IV | N = 12 | N = 12 | N = 12 |
| (N = 14) | 45.1 sec | 93.4 sec* | 87.5 sec* |
| | (−75 to 237) | (0 to 285) | (−60 to 285) |
| ALL GROUPS | N = 40 | N = 43 | N = 35 |
| (N = 66) | 45.0 sec | 96.0 sec | 100.0 sec |

N = number of subjects;
mean; (range in seconds);
*= p < 0.05

Referring to Table 1, the mean change from baseline at one month was less than 60 seconds for all dose groups. However, the percentage of patients stopping their treadmill test because of angina decreased in all groups over time. At 2 months and 6 months after dosing, the mean changes from baseline were greater in the high dose IC and IV groups of patients than in the low and mid dose IC groups. The persistence of increased ETT at 6 months (133.1 sec and 87.5 sec) in the high dose IC (24-48 μg/kg) and IV (18 & 38 μg/kg) groups, respectively, was unexpected. The greatest mean increases in ETT of 107.9 and 133.1 seconds at 2 and 6 months, respectively, occurred in the high dose (24-48 μg/kg) IC group. The IV group exhibited significant mean increases in ETT of 93.4 seconds and 87.5 seconds, at 2 months and 6 months respectively, which was not predicted by the rat and pig animal models used herein. Overall, the persistence of the effect (increase in ETT) at six months and its magnitude for both the IC and IV groups was wholly unexpected.

The 66 human patients of the Phase I clinical trial described in Examples 1-3 herein were also evaluated using the Seattle Angina Questionnaire (SAQ). The SAQ is a validated, disease-specific, quality of life instrument which assesses the following five scales: 1) "exertional capacity"=limitation of physical activity; 2) "disease perception"=worry about MI; 3) "treatment satisfaction"; 4) "angina frequency"=number of episodes and sublingual nitroglycerin usage; and 5) "angina stability"=number of episodes with most strenuous physical activity. The possible range of scores for each of the five scales is 0 to 100 with the higher scores indicating a better quality of life. Typically, a mean change of 8 points or more between the mean baseline scores (i.e., before treatment) and the post-treatment scores is recognized as being "clinically significant." However, in the present analysis, a dose was considered "effective" if the mean change in score from baseline increased by greater than 14 points. The reason that 14 was chosen (instead of 8) was to allow for the improvement that was seen in the placebo group at 2 months in a clinical trial of another growth factor—VEGF.

In performing the SAQ evaluation, the patients were categorized according to the same dosage groups that were evaluated for ETT, i.e., 0.33-2.0 μg/kg IC (low) 6.0-12.0

μg/kg IC (mid); 24-48 μg/kg IC (high); and 18 and 36 μg/kg IV. The questionnaire was administered to subjects in each dosage group at baseline (prior to dosing), and at 2 months and 6 months after being administered a single unit dose composition of rFGF-2 in accordance with the method of the present invention.

The first SAQ scale is "exertional capacity." The data on exertional capacity is summarized in Table 2 herein.

TABLE 2

Exertional Capacity (EC) - Change from Baseline

| FGF-2 Dose Group | Change from Baseline at Two Months | Change from Baseline at Six Months |
|---|---|---|
| 0.33 to 2.0 μg/kg IC (N = 16) | N = 14 15.0* (−25 to 53) | N = 7 23.2* (0 to 53) |
| 6.0 and 12 μg/kg IC (N = 8) | N = 7 20.2* (−14 to 44) | N = 6 24.1 (−11 to 69) |
| 24.0 to 48.0 μg/kg IC (N = 28) | N = 26 14.6* (−33 to 75) | N = 23 22.9* (−14 to 75) |
| 18.0 and 36.0 μg/kg IV (N = 14) | N = 12 10.9 (−8 to 67) | N = 14 16.5* (−19 to 63) |

N = number of subjects;
mean (range);
*= p < 0.05

As reflected in Table 2, the change from baseline in mean score increased at 2 and 6 months for each of the three IC dosage groups and at 6 months for all dosage groups (IC and IV). All scores at all dosage levels increased with time in going from 2 months to 6 months with the best increases (23.2, 24.1, 22.9 and 16.5) relative to baseline being seen at 6 months post-dosing.

The second SAQ scale to be evaluated was "angina stability." The data summarizing the angina stability is presented in Table 3 herein.

TABLE 3

Angina Stability (AS) - Change from Baseline

| FGF-2 Dose Group | Change from Baseline at Two Months | Change from Baseline at Six Months |
|---|---|---|
| 0.33 to 2.0 μg/kg IC (N = 16) | N = 13 46.2* (0 to 100) | N = 7 21.4* (0 to 50) |
| 6.0 and 12 μg/kg IC (N = 8) | N = 7 32.1* (0 to 50) | N = 6 16.7 (−25 to 50) |
| 24.0 to 48.0 μg/kg IC (N = 28) | N = 27 34.3* (−25 to 75) | N = 24 17.7* (−25 to 75) |
| 18.0 and 36.0 μg/kg IV (N = 14) | N = 12 39.6* (0 to 100) | N = 14 23.2* (0 to 75) |

N = number of subjects;
mean (range);
*= p < 0.05

According to Table 3, the change in score for angina stability increased relative to baseline at both 2 and 6 months for each group. The improvements in angina stability seen at 2 months after dosing (46.2, 32.1, 34.3 and 39.6) were significantly greater than those scores seen at 6 months (21.4, 16.7, 17.7 and 23.2). However, the scores found at both 2 months and 6 months after dosing showed that all dosages were found to be effective (>14) in increasing angina stability. Moreover, the magnitude of the increases and their duration for 6 months were unexpected.

The third SAQ scale to be evaluated was "angina frequency." The data summarizing the angina frequency is presented in Table 4 herein.

TABLE 4

Angina Frequency (AF) - Change from Baseline

| FGF-2 Dose Group | Change from Baseline at Two Months | Change from Baseline at Six Months |
|---|---|---|
| 0.33 to 2.0 μg/kg IC (N = 16) (low) | N = 14 27.9* (−10 to 80) | N = 7 12.9 (−40 to 50) |
| 6.0 and 12 μg/kg IC (N = 8) (mid) | N = 7 32.9* (0 to 80) | N = 6 36.7 (−10 to 90) |
| 24.0 to 48.0 μg/kg IC (N = 28) (high) | N = 27 28.9* (−40 to 80) | N = 24 25.8* (−30 to 80) |
| 18.0 and 36.0 μg/kg IV (N = 14) | N = 12 20.0* (0 to 90) | N = 14 11.4 (−30 to 60) |
| ALL GROUPS (N = 66) | N = 60 27.3 | N = 51 21.4 |

N = number of subjects;
mean (range);
*= p < 0.05

According to Table 4, the mean patient scores (27.9, 32.9, 28.9 and 20.0) for angina frequency increased at 2 months (relative to baseline) by an effective amount (>14) for all dosage groups and for all modes of administration (IC or IV). The mean patient scores continued to increase at 6 months only for the mid dose (6.0-12.0 μg/kg) group, suggesting a peak effect at 2 months post-dosing. However, for the mid dose (6.0-12.0 μg/kg) and high dose (24.0-48.0 μg/kg) groups, the changes at 2 months and 6 months were similar, suggesting a persistent effect at 6 months on angina frequency. The third SAQ scale to be evaluated was "angina frequency." The data summarizing the angina frequency is presented in Table 4 herein.

The fourth SAQ scale to be evaluated was "angina frequency." The data summarizing the angina frequency is presented in Table 5 herein.

TABLE 5

Treatment Satisfaction (TS) - Change from Baseline

| FGF-2 Dose Group | Change from Baseline at Two Months | Change from Baseline at Six Months |
|---|---|---|
| 0.33 to 2.0 μg/kg IC (N = 16) (low) | N = 14 8.5* (−19 to 31) | N = 7 6.3 (−25 to 25) |
| 6.0 and 12 μg/kg IC (N = 8) (mid) | N = 7 17.9 (−13 to 44) | N = 6 19.8 (0 to 63) |
| 24.0 to 48.0 μg/kg IC (N = 28) (high) | N = 27 18.8* (−38 to 69) | N = 24 13.0 (−75 to 63) |
| 18.0 and 36.0 μg/kg IV (N = 14) | N = 12 19.8* (−13 to 63) | N = 14 13.4* (−19 to 56) |

N = number of subjects;
mean (range);
*= p < 0.05

According to Table 5, the score for treatment satisfaction increased by an effective amount at 2 months for the mid and high dose IC groups as well as the IV group. At six months post-dosing, only the score for the mid dose group IC had a score that was greater than 14, suggesting a peak effect for treatment satisfaction at 2 months.

The fifth SAQ scale to be evaluated was "disease perception." The data summarizing the disease perception is presented in Table 6 herein. According to Table 6, the scores for disease perception increased from baseline to scores of 20.2-29.2 at 2 months and 23.8-34.0 at 6 months. These scores showed that administering a single unit dose composition in accordance with the method of the present invention was considered to be as effective (or more effective) at 6 months as at two months. These scores suggest a persistence of the effectiveness of the method of the present invention on disease perception out to six months following administration of a single unit dose composition.

TABLE 6

Disease Perception (DP) - Change from Baseline

| Dose Group | Change from Baseline at Two Months | Change from Baseline at Six Months |
| --- | --- | --- |
| 0.33 to 2.0 µg/kg IC (N = 16) (low) | N = 14 29.2* (−8 to 58) | N = 7 26.2* (0 to 42) |
| 6.0 and 12 µg/kg IC (N = 8) (mid) | N = 7 20.2* (−8 to 50) | N = 6 30.6* (0 to 58) |
| 24.0 to 48.0 µg/kg IC (N = 28) (high) | N = 27 27.8* (−33 to 92) | N = 24 34.0* (−33 to 100) |
| 18.0 and 36.0 µg/kg IV (N = 14) | N = 12 22.9* (−8 to 92) | N = 14 23.8* (−8 to 75) |

N = number of subjects;
mean (range);
*= p < 0.05

Up to 60 of the human patients of the Phase I clinical trial described in Examples 1-3 herein were also evaluated using resting magnetic resonance imaging (MRI) scans of their heart. The resting MRI scans were performed on the patients at baseline, and at 1 month, 2 months and 6 months after dosing with a single unit dose composition of the present invention. The doses were considered "effective" based upon statistical significance ($p<0.05$). The objective criteria assessed by the resting MRI scans are the following: (1) ejection fraction; (2) myocardial infarct extent (%); (3) normal wall thickening (4) normal wall motion (%); (5) target wall thickening (%); (6) target wall motion (%); (7) target wall area collateral extent (%); and (8) target area delayed arrival extent (%).

Based upon the resting MRI, no change in "ejection fraction" was observed at one month for any one group. The mean change from baseline for all groups (n=33) at 1 month was an increase of 2.0% (p=0.042). At two months, the mean change from baseline for the low dose IC group (n=13) was an increase of 8.1% (p=0.007); and for all groups (n=54), the mean change from baseline was an increase of 3.8% (p=0.001). At six months, the mean change from baseline for the high dose IC group (n=19) was 5.3% (p=0.023); for the IV group (n=3) was 11.1% (p=0.087); and for all groups (n=33) was 5.7% (p=0.001).

Based upon the resting MRI, there was no statistically significant change in the "myocardial infarct extent" (%) for any group, or for all groups in combination at 1 month, 2 months or 6 months post-dosing. When the normal wall motion (%) and normal wall thickening were assessed, there was no statistically significant change from baseline at 1 month, 2 months or 6 months for any one group. However, there was a statistically significant change from baseline in target wall motion for all groups at one (n=60), two (n=54) and six (n=33) months, which was reflected as a mean increase from baseline of 2.7% (p=0.015), 4.4% (p=<0.001) and 6.4% (p<0.001), respectively. However, there was also a statistically significant change from baseline in target wall thickening for all groups at one (n=60), two (n=54) and six (n=33) months, which was reflected as a mean increase from baseline of 4.4% (p=0.015), 6.3% (p=<0.001) and 7.7% (p<0.001), respectively.

The next criteria assessed by MRI was "target area collateral extent" (%). The mean increase from baseline in target area collateral extent for all groups was highly statistically significant at one month (n=31), two months (n=27) and six months (n=16), wherein the increases were 8.3% (p<0.001), 10.9% (p<0.001) and 11.2% (p<0.001), respectively. The greatest collateral extent increases were observed for the low and mid IC doses, i.e., at one month (10.4% and 18.3%, respectively), two months (14.7% and 18.0%, respectively) and six months (16.0% and no value for mid dose, respectively), which was wholly unexpected. At one month, two months and six months post-dosing, the corresponding % increases in target area collateral extent that were observed for the IC high dose group were 6.3%, 8.0% and 9.0%, respectively.

The final criteria assessed by MRI was "target area delayed arrival extent" (%). The mean decrease from baseline in target area delayed arrival extent for all groups was highly statistically significant at 1 month (n=60), 2 months (n=54) and 6 months (n=34), wherein the decreases were −5.8% (p<0.001), −8.3% (p<0.001) and −10.0% (p<0.001), respectively. The greatest target area delayed extent decreases were observed for the low dose IC group, which was also highly unexpected.

Thus, providing CAD patients with a single IC or IV infusion of rFGF-2 in accordance with the present invention provided the patients with a statistically significant physical improvement as objectively measured by MRI and other conventional criteria.

Pharmacokinetics and Metabolism

The molecular structure of FGF-2 contains a positively charged tail that is known to bind to proteoglycan chains (heparin and heparin-like structures) on cell surfaces and on the endothelial wall of the vasculature. See Moscatelli, et al., "*Interaction of Basic Fibroblast Growth Factor with Extracellular Matrix and Receptors*," Ann. NY Acad. Sci., 638: 177-181 (1981).

The kidneys and liver are the major organs for the elimination of rFGF-2. In particular, the kidneys have a protein cutoff of about 60 kD and thus retain serum albumin (MW 60 kD). However, FGF-2 (146 residues) has a molecular weight of about 16.5 kD. Accordingly, renal excretion is to be expected. In a radiolabelled biodistribution study of commercially available bovine FGF-2 (bFGF-2), both the liver and the kidney were shown to contain high counts of the radiolabelled bFGF-2 at 1 hour after IV or IC injection. In a published study, wherein another recombinant iodinated form of bFGF-2 was given to rats, the liver was identified as the major organ of elimination. Whalen et al., "*The Fate of Intravenously Administered bFGF and the Effect of Heparin*," Growth Factors, 1:157-164 (1989). It is also known that FGF-2 binds in the general circulation to $\alpha_2$-macroglobulin and that this complex is internalized by receptors on the Kupffer cells. Whalen et al. (1989) and LaMarre et al., "*Cytokine Binding and Clearance Properties of Proteinase-Activated Alpha-2-Macroglobulins*," Lab. Invest., 65:3-14 (1991). Labelled FGF-2 fragments were not found in the plasma, but they were found in the urine and corresponded in size to intracellular breakdown products.

In preclinical testing, we determined the pharmacokinetics of rFGF-2 (SEQ ID NO:2) after intravenous (IV) and intracoronary (IC) administration in domestic Yorkshire pigs, and after IV administration dosing in Sprague Dawley ("SD") rats. The pig models demonstrated linear pharmacokinetics (0.65 µg/kg-20 µg/kg) IC and IV. The terminal half-life of the FGF-2 in the pig model was 3-4 hours. The rat models demonstrated linear pharmacokinetics over the range of 30-300 µg/kg IV. The terminal half-life of the FGF-2 in the rat model was 1 hour. Both species showed plasma concentration suggesting a two-compartment model.

Likewise, in humans, the FGF-2 plasma concentrations after IV and/or IC infusion followed a biexponential curve with an initial steep slope and considerable decrease over several log scales (the distribution phase) during the first hour, followed by a more moderate decline (the elimination phase). FIG. 1A provides a plasma concentration versus time curve showing these phases in humans after IC administration of rFGF-2 of SEQ ID NO:2 as a function of each of the following eight doses: 0.33 µg/kg, 0.65 µg/kg, 2 µg/kg, 6 µg/kg, 12 µg/kg, 24 µg/kg, 36 µg/kg, and 48 µg/kg of lean body mass (LBM). FIG. 1A shows the plasma dose linearity for the eight doses of rFGF-2 that were administered by IC infusion over a twenty minute period. FIG. 1A also shows a biphasic plasma level decline, i.e., a fast distribution phase during the first hour, followed by an elimination phase with an estimated $T_{1/2}$ of 5-7 hours. The plasma concentrations of FGF-2 of SEQ ID NO:2 were determined by a commercially available ELISA (R&D Systems, Minneapolis Minn.) that was marketed for analysis of human FGF-2. The ELISA assay showed 100% cross-reactivity with the rFGF-2 of SEQ ID NO:2. Other members of the FGF family, as well as many other cytokines, were not detected by this assay. Further, heparin does not interfere with the assay.

Figure 1B:
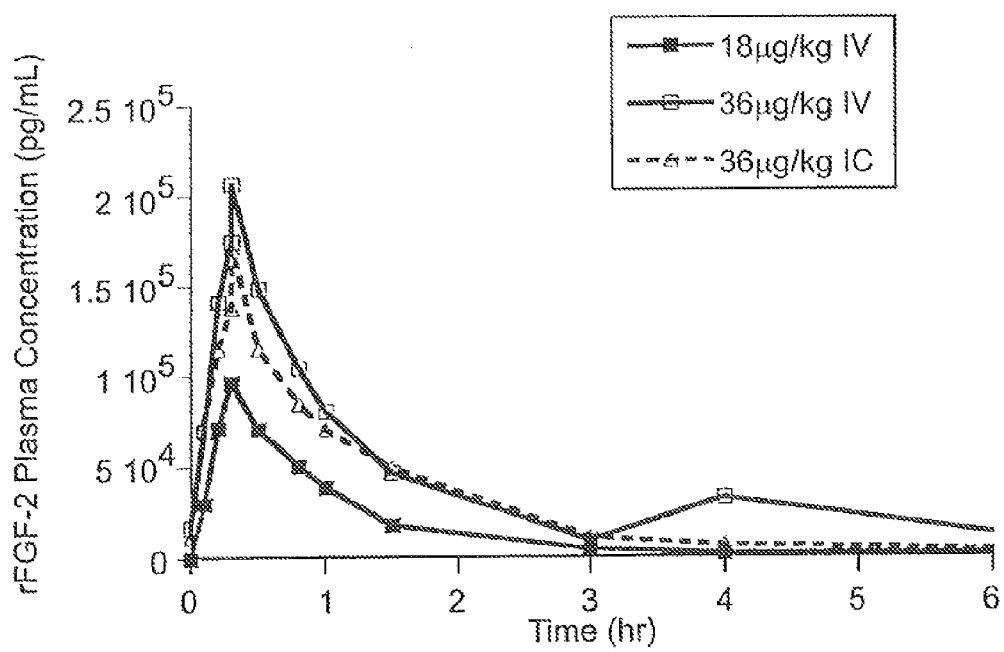
FIG. 1B is a plot of the mean FGF-2 plasma concentration versus time profiles for 2 different doses of rFGF-2 (SEQ ID NO:2) administered by IV infusion in humans over a 20 minute period. The two IV doses of rFGF-2 in FIG. 1B are 18 and 36 µg/kg. The mean concentration-time profile following IC administration of 36 µg/kg rFGF-2 is included for comparison.

FIG. 1B is a plot of the mean FGF-2 plasma concentration as a function of time for 18 µg/kg and 36 µg/kg rFGF-2 administered IV, as compared to 36 µg/kg rFGF-2 administered IC. The plasma concentration versus time profiles in FIG. 1B for the 36 µg/kg doses by the IV and IC routes are superimposible. However, a first-pass effect with the IC route is not eliminated.

FIG. 2 is a plot of mean FGF-2 area under the curve (AUC) in pg*min/ml corresponding to FIGS. 1A and 1B. FIG. 2 shows the dose linearity of systemic rFGF-2 exposure (AUC) following IC or IV infusion. In particular, FIG. 2 shows that the systemic exposure to rFGF-2 following administration by the IC and IV routes is substantially similar.

FIG. 3 is a plot of individual human patient plasma clearance (CL) values (ml/min/kg) as a function of the time of heparin administration in "minutes prior to rFGF-2 infusion." FIG. 3 shows the influence of timing of heparin administration on FGF-2 plasma clearance (CL). Although FIG. 3 shows that administering heparin up to 100 minutes prior to rFGF-2 decreases FGF-2 clearance, the preferred time for administering heparin is from 0-30 minutes prior the rFGF-2 administration, wherein the effect of the heparin on decreasing FGF-2 clearance is greatest.

Figure 4:
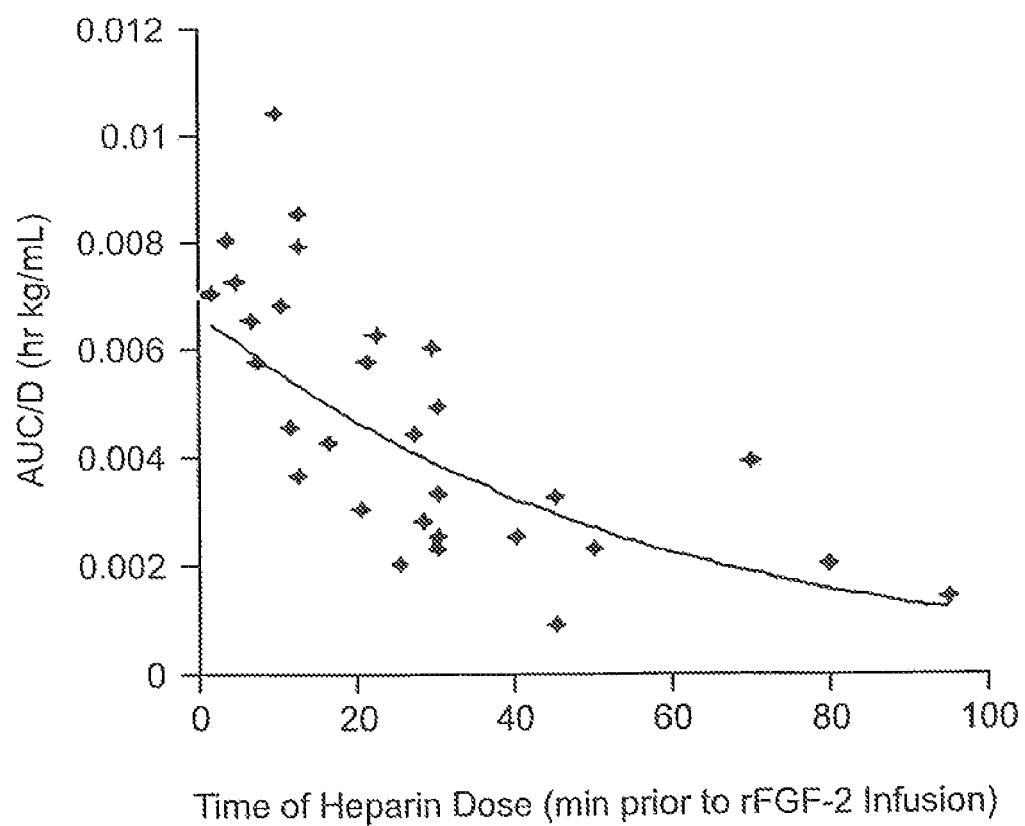
FIG. 4 is a plot individual human patient FGF-2 dose normalized area under curves (AUCs) as a function of the time of heparin administration in "minutes prior to rFGF-2 infusion" and shows the influence of timing of heparin administration on FGF-2 AUC.

FIG. 4 is a plot OF individual human patient rFGF-2 dose normalized area under curves (AUCs) as a function of the time of heparin administration in "minutes prior to rFGF-2 infusion" and shows the influence of timing of heparin administration on rFGF-2 AUC. FIG. 4 shows that the greatest AUC/dose was achieved when an effective amount of a glycosoaminoglycan, such as heparin, was preadministered within 30 minutes or less of IC rFGF-2 infusion, more preferably within 20 minutes or less of IC or IV rFGF-2 infusion. Typically, an effective amount of a glycosoaminoglycan is 10-80 U/kg heparin.

The mean pharmacokinetic parameters for rFGF-2 in humans as a function of dosage and mode of administration are summarized in Table 8 herein. Referring to Table 8, the T½ for FGF-2 in humans was determined to range from 2.2±3.7 hours at low dose (0.33-2.0 µg/kg) IC to 7.0±3.5 hours at a dose of 18-36 µg/kg IV; given the limitations of the assay, the terminal half-life is estimated at 5-7 hours for all groups. The clearances of FGF-2 ranged from 13.2 to 18.2 L/hour/70 kg man. Finally, the steady state volume ($V_{ss}$) was determined to range from 11.3±10.4 L/70 kg man to 16.8±10.7 L/70 kg man.

TABLE 8

Mean rFGF-2 PK Parameters in Humans

| FGF-2 Dose µg/kg | N | Route | CL (L/hr/70 kg) | $t_{1/2}$ (h) | $V_{ss}$ (L/70 kg) |
|---|---|---|---|---|---|
| 0.3-2 | 16 | IC | 18.2 ± 13.4 | 2.2 ± 3.7 | 11.3 ± 10.4 |
| 6-12 | 8 | IC | 13.2 ± 7.3 | 3.1 ± 2.5 | 12.1 ± 4.9 |
| 24-48 | 28 | IC | 14.7 ± 8.3 | 6.3 ± 1.8 | 16.8 ± 10.7 |
| 18-36 | 14 | IV | 13.9 ± 7.9 | 7.0 ± 3.5 | 16.4 ± 8.6 |

Although the binding of FGF-2 to heparin-like structures is strong (dissociation constant ~2×10$^{-9}$ M), the binding of FGF-2 to a specific tyrosine kinase receptor is approximately two orders of magnitude higher (dissociation constant ~2×10$^{-11}$ M). Moscatelli et al., (1991). Thus, without being bound to any theory, the complexation of rFGF-2 with a glycosoaminoglycan, such as a heparin, might increase signal transduction and mitogenesis, and/or protect the rFGF-2 from enzymatic degradation.

The examples, which follow, provide more details on the selection criterion and the Phase I clinical trial that gave rise to the data discussed above.

Example 1

Unit Dose of rFGF-2 Employed in the Phase I Clinical Trial

The rFGF-2 of SEQ ID NO:2 was formulated as a unit dose and pharmaceutical composition and administered to rats, pigs and ultimately to humans in the Phase I clinical trial referenced herein. The various formulations are described below.

The rFGF-2 unit dose was provided as a liquid in 3 cc type I glass vials with a laminated gray butyl rubber stopper and red flip-off overseal. The rFGF-2 unit dose contained 1.2 ml of 0.3 mg/ml rFGF-2 of SEQ ID NO:2 in 10 mM sodium citrate, 10 mM monothioglycerol, 1 mM disodium dihydrate EDTA (molecular weight 372.2), 135 mM sodium chloride, pH 5.0. Thus, in absolute terms, each vial (and unit dose) contained 0.36 mg rFGF-2. The vials containing the unit dose in liquid form were stored at 2° to 8° C.

The rFGF diluent was supplied in 5 cc type I glass vials with a laminated gray butyl rubber stopper and red flip-off overseal. The rFGF-2 diluent contains 10 mM sodium citrate, 10 mM monothioglycerol, 135 mM sodium chloride, pH 5.0. Each vial contained 5.2 ml of rFGF-2 diluent solution that was stored at 2° to 8° C.

The rFGF-2 pharmaceutical composition that was infused was prepared by diluting the rFGF-2 unit dose with the rFGF diluent such that the infusion volume is 10-40 ml. In order to keep the EDTA concentration below a preset limit of 100 µg/ml, the total infusion volume was increased to a maximum of 40 ml when proportionately higher absolute amounts of FGF-2 were administered to patients with higher body weights.

Example 2

Selection Criteria for Patients with Coronary Artery Disease for Treatment with rFGF-2

The following selection criteria were applied to Phase I patients with coronary artery disease, whose activities were limited by coronary ischemia despite optimal medical management, and who were not candidates for approved revascularization therapies:

Inclusion Criteria:
Subject is eligible if:
Male or female, greater than or equal to 18 years of age
Diagnosis of coronary artery disease (CAD)
Suboptimal candidates for approved revascularization procedures, e.g., angioplasty, stents, coronary artery bypass graft (CABG) (or refuses those interventions)
Able to exercise at least three minutes using a modified Bruce protocol and limited by coronary ischemia
Inducible and reversible defect of at least 20% myocardium on pharmacologically stressed thallium sestamibi scan
CBC, platelets, serum chemistry within clinically acceptable range for required cardiac catheterization
Normal INR, or if anticoagulated with Coumadin, INR<2.0
Willing and able to give written informed consent to participate in this study, including all required study procedures and follow-up visits
Exclusion Criteria:
Subject is not eligible if:
Malignancy: any history of malignancy within past ten years, with the exception of curatively treated basal cell carcinoma
Ocular conditions: proliferative retinopathy, severe non-proliferative retinopathy, retinal vein occlusion, Eales' disease, or macular edema or funduscopy by ophthalmologist: history of intraocular surgery within six months
Renal function: creatinine clearance below normal range adjusted for age; protein>250 mg or microalbumin>30 mg/24 h urine
Class IV heart failure (New York Heart Association)
Ejection fraction<20% by echocardiogram, thallium scan, MRI or gated pooled blood scan (MUGA)
Hemodynamically relevant arrhythmias (e.g., ventricular fibrillation, sustained ventricular tachycardia)
Severe valvular stenosis (aortic area<1.0 $cm^2$, mitral area<1.2 $cm^2$), or severe valvular insufficiency
Marked increase in angina or unstable angina within three weeks
History of myocardial infarction (MI) within three months
History of transient ischemic attack (TIA) or stroke within six months
History of CABG, angioplasty or stent within six months
History of treatment with transmyocardial laser revascularization, rFGF-2, or vascular enodothelial growth factor (VEGF) within six months
Females of child-bearing potential or nursing mothers
Any pathological fibrosis, e.g., pulmonary fibrosis, scleroderma
Known vascular malformation, e.g., AV malformation, hemangiomas
Coexistence of any disease which might interfere with assessment of symptoms of CAD, e.g., pericarditis, costochondritis, esophagitis, systemic vasculitis, sickle cell disease
Coexistence of any disease which limits performance of modified Bruce protocol exercise stress test, e.g., paralysis or amputation of a lower extremity, severe arthritis or lower extremities, severe chronic obstructive pulmonary disease (COPD)
Participation in clinical trials of investigational agents, devices or procedures within thirty days (or scheduled within sixty days of study drug)
Known hypersensitivity to rFGF-2 or related compounds
Any condition which makes the subject unsuitable for participation in this study in the opinion of the investigator, e.g., psychosis, severe mental retardation, inability to communicate with study personnel, drug or alcohol abuse.

Example 3

Phase I Clinical Study on Recombinant FGF-2 (SEQ ID NO:2) Administered to Humans The Phase I CAD trial of this example is an open label, dose escalation study of recombinant fibroblast growth factor-2 (rFGF-2) for safety, tolerability and pharmacokinetics. The study was conducted at two sites: Beth Israel Deaconess Hospital (Harvard) in Boston, Mass. and Emory University Hospital in Atlanta, Ga. Enrollment is complete. Subjects were treated with a single infusion of rFGF-2 on Day 1 and followed for 360 days; follow-up is not yet complete in some subjects.

The subject population consists of patients with advanced CAD who are exercise limited by coronary ischemia and are considered suboptimal candidates for (or do not want to undergo) one of the established revascularization procedures (e.g., CABG, angioplasty—with or without stent). The major exclusion criteria were history or suspicion of malignancy, uncompensated heart failure or left ventricular ejection fraction<20%, renal insufficiency or proteinuria, and various ocular conditions (e.g., proliferative diabetic retinopathy, severe non-proliferative retinopathy).

Sixty-six subjects have received rFGF-2 of SEQ ID NO:2 in this trial: fifty-two received the rFGF-2 as an IC infusion and fourteen received it as an IV infusion. Each subject was observed in the hospital for at least twenty-four hours, and then followed as an outpatient for 360 days with follow-up visits (Days 15, 29, 57, 180 and 360). At least four subjects were studied at each dose; if no subject experienced dose-limiting toxicity as defined by the protocol within six days, the dose was escalated. The drug was administered as a single 20 minute infusion divided between two major sources of coronary blood supply (IC), using standard techniques for positioning a catheter into the patient's coronary artery (such as already employed in angioplasty) or in a peripheral vein (IV). The doses in µg/kg of rFGF-2 administered IC (and the number of patients) were 0.33 (n=4), 0.65 (n=4), 2.0 (n=8), 6.0 (n=4), 12.0 (n=4), 24 (n=8), 36 (n=10) and 48 (n=10) of rFGF-2 of SEQ ID NO:2. The doses in µg/kg of rFGF-2 administered IV (and the number of patients) were 18.0 (n=4) and 36.0 (n=10) or rFGF-2 of SEQ ID NO: 2.

Angina frequency and quality of life was assessed by the Seattle Angina Questionnaire (SAQ) at a baseline (before rFGF-2 administration) and at 2 months and 6 months after rFGF-2 administration. Exercise tolerance time (ETT) was assessed by the treadmill test at 1, 2, and 6 months. Rest/exercise nuclear perfusion and gated sestamibi-determined rest ejection fraction (EF), and resting magnetic resonance imaging (MRI) were assessed at baseline, and at 1 month, 2 months and 6 months post rFGF-2 administration. MRI measurements which were thought to objectively measure changes in % in cardiac function and perfusion included: (1) ejection fraction; (2) myocardial infarct extent (%); (3) normal wall thickening (4) normal motion (%); (5) target wall thickening (%); (6) target wall motion (%); (7) target wall area collateral extent (%); and (8) target area delayed arrival extent (%).

If one of four subjects experienced dose-limiting toxicity (as defined by the protocol), four additional subjects were studied at that dose; if none experienced toxicity, the dose was escalated and another group was studied. The maximally tolerated dose (MTD) was defined as the IC dose which was tolerated by 9/10 subjects, i.e., 36 µg/kg IC.

Careful fluid management pre-infusion was prescribed using a Swan-Ganz catheter and vital signs were monitored frequently during dosing. Heparin was administered IV prior to the infusion of rFGF-2 in all groups. The EDTA concentration was less than 100 µg/ml in the unit dose composition. Volume of study drug administered varied with dose and subject's weight, and ranged from 10 ml at lower doses to 40 ml at higher doses.

Preliminary Results

The results presented here are unaudited and are based on a third interim analysis for sixty-six subjects with six months follow-up for all groups (1-10) and the serious adverse events (SAE) report of 29 Jul. 1999 from Chiron Drug Safety. Data collection for the last visit (Day 360) and final analysis is in progress.

The starting dose of 0.33 µg/kg IC was escalated over eight sequential groups to 48 µg/kg IC, at which dose 2 of ten subjects experienced dose-limiting toxicity (hypotension) as defined by the protocol. Hypotension was manageable with fluids alone in all subjects (no vasopressors or assistive devices). At 36 µg/kg IC, only 1 of 10 subjects had dose-limiting toxicity which defined this dose as the maximally tolerated dose (MTD). Two additional groups were studied by IV infusion; four subjects of half the MTD (18 µg/kg) and ten subjects at the MTD (36 µg/kg).

Hypotension was dose-limiting in humans, as predicted by the animal model in Yorkshire pigs. However, 36.0 µg/kg rFGF-2 IC was tolerated in humans; whereas in pigs, 20.0 µg/kg rFGF-2 IC caused profound hypotension in one of two animals. Better tolerability in humans was attributed to aggressive fluid management and absence of general anesthesia.

As of 29 Jul. 1999, thirty-three serious adverse events (SAEs) have occurred in 24/66 subjects, but were not dose-related. Fifteen (15) SAEs were considered at least possibly related to rFGF-2; whenever there was a difference between relatedness assigned by the investigator and the medical monitor, the more conservative relationship was assigned. SAE's were multiple in five subjects: 01103 (0.33 µg/kg IC), 01106 (0.65 µg/kg IC), 01113 (2.0 µg/kg IC), 01137 (36.0 µg/kg IV), 02101 (0.65 µg/kg IC).

The most frequent treatment-emergent adverse events (AEs) on Day 1 were transient systolic hypotension and transient bradycardia. The hypotension was dose-dependent and occurred more frequently at doses greater than or equal to (≥) 24 µg/kg IC; bradycardia was not dose-dependent. Other adverse events (AEs) which were deemed at least possibly related and appeared dose-related occurred within the first several days or week post infusion and included chest pain, shortness of breath, insomnia, anxiety, and nausea. These events were mild to moderate in severity, and most did not require specific intervention.

When administered IC, the drug was administered over approximately 20 minutes as a single infusion divided between two major sources of coronary blood supply (IC), using standard techniques for positioning a catheter into the patient's coronary artery (such as already employed in angioplasty). When administered IV, the drug was administered as an infusion over 20 minutes into a peripheral vein.

The preliminary safety results indicate that serious events were not dose related. Thus far, of the eight IC dosage groups, there were three deaths in the lower dosage groups, i.e., at 0.65 µg/kg (Day 23), at 2.0 µg/kg (Day 57) and at 6.0 µg/kg (Day 63), and one death in the highest dose group, i.e., at 48.0 µg/kg (approximately 4 months post-dosing). Three of the deaths were cardiac; one death was due to a large B cell lymphoma that was diagnosed three weeks after dosing in the patient in group 4 (6.0 µg/kg) who patient died at two months post-dosing.

Acute myocardial infarction (MI) occurred in four patients, i.e., one patient from each of groups 1 (0.33 µg/kg), 3 (2.0 µg/kg), 4 (6.0 µg/kg) and 7 (36.0 µg/kg). Multiple MIs occurred in two patients, i.e., one from group 1 (0.33 µg/kg) and one from group 3 (2.0 µg/kg). Emergency revascularization procedures (CABG or angioplasty with or without stent) were performed during follow-up in 4 patients: one each from groups 1 (0.33 µg/kg), 3 (2.0 µg/kg), 4 (6.0 µg/kg), and 7 (36.0 µg/kg).

Acute hypotension, seen at higher doses during or just subsequent to infusion, was managed by administration of IV fluids without need for a vasopressor. The maximally tolerated dose (MTD) in humans was defined as 36 µg/kg IC. (In contrast, in pigs, the MTD was 6.5 µg/kg IC.) Doses of rFGF-2 up to 48 µg/kg IC were administered in human patients with aggressive fluid management, but were defined by the protocol as "not tolerated" due to acute and/or orthostatic hypotension in two out of ten patients. The terminal half-life of the infused rFGF-2 was estimated at 5 to 7 hours.

The human patients in this study that were treated with a single IC or IV infusion of rFGF-2 of SEQ ID NO:2 exhibited a mean increase in ETT of 1.5 to 2 minutes. See Table 1. This is especially significant because an increase in ETT of greater than (>) 30 seconds is considered significant and a benchmark for evaluating alternative therapies, such as angioplasty. The angina frequency and quality of life, as measured by SAQ, showed a significant improvement at 2 months in all five subscales for the 66 patients (n=66) tested. See Tables 26. In Tables 2-6, a mean change of 14 or more was considered "clinically significant."

When 33 human CAD patients were assessed by resting cardiac magnetic resonance imaging (MRI) at baseline, and at 1, 2, and 6 months after receiving a single unit dose composition of the present invention by IC or IV routes, a highly statistically significant increase was observed in target wall thickening, target wall motion and target area collateral extent; a highly statistically significant decrease was observed in target area delayed arrival extent; and no statistically significant changes were observed in normal wall motion, normal wall thickening or myocardial infarct extent.

In addition to the above criterion (i.e., ETT, SAQ, MRI), a treatment is considered very successful if the angiogenic effects last at least six months. In the present Phase I study, the unexpectedly superior angiogenic effects were observed to last up to 6 months in some patients in all dosage groups. Based upon the results already obtained, it is expected that the angiogenic effects may last twelve months or more but do last at least six months in the patients, at which time the procedure could be repeated, if necessary.

Example 4

Proposed Phase II Clinical Study on rFGF-2 (SEQ ID NO:2) Administered to Humans to Treat Coronary Artery Disease The Phase II clinical trial of rFGF-2 for treating human patients for coronary artery disease is performed as a double blind/placebo controlled study having four arms: placebo, 0.3 µg/kg, 3.0 µg/kg, and 30 µg/kg administered once IC. This study is ongoing and results are not yet available.

Example 5

Unit Dose and Pharmaceutical Composition of rFGF-2 for the Phase II Human Clinical Trial The rFGF-2 of SEQ ID NO:2 was formulated as a unit dose pharmaceutical composition for administration to humans in the Phase II clinical trial referenced herein. The various formulations are described below.

The rFGF-2 unit dose was prepared as a liquid in 5 cc type I glass vials with a laminated gray butyl rubber stopper and red flip-off overseal. The rFGF-2 formulation contains 0.3 mg/ml rFGF-2 of SEQ ID NO:2 in 10 mM sodium citrate, 10 mM monothioglycerol, 0.3 mM disodium dihydrate EDTA (molecular weight 372.2), 135 mM sodium chloride, pH 5.0. Each vial contained 3.7 ml of rFGF-2 drug product solution (1.11 mg rFGF-2 per vial). The resulting unit dose in liquid form is stored at less than −60° C. The above described unit dose is diluted with the "rFGF-2 placebo." Depending on the size of the patient, the contents of several of the vials may be combined to produce a unit dose of 36 µg/kg for the Phase II study.

The rFGF-2 placebo is supplied as a clear colorless liquid in 5 cc type I glass vials with a laminated gray butyl rubber stopper and red flip-off overseal. The rFGF-2 placebo is indistinguishable in appearance from the drug product and has the following formulation: 10 mM sodium citrate, 10 mM monothioglycerol, 0.3 mM disodium dihydrate EDTA (molecular weight 372.2), 135 mM sodium chloride, pH 5.0. Each vial contains 5.2 ml of rFGF-2 placebo solution. Unlike the unit dose, the rFGF-2 placebo is stored at 2° to 8° C.

The rFGF-2 pharmaceutical composition that is infused is prepared by diluting the rFGF-2 unit dose with the rFGF diluent such that the infusion volume is 20 ml for Phase II.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the present invention described herein.

---

What is claimed is:

1. A method for treating a human patient for coronary artery disease, comprising:
   administering a therapeutically effective amount of a recombinant fibroblast growth factor-2 (FGF-2) or an angiogenically active, terminally truncated fragment of said FGF-2 into one or more coronary vessels or into a peripheral vein in a human patient in need of treatment for said coronary artery disease, wherein said therapeutically effective amount is about 0.2 µg/kg to 48 µg/kg of patient weight;
   wherein said recombinant FGF-2 is human FGF-2 and has the amino acid sequence set forth in SEQ ID NO: 2 with a threonine residue substituted for the serine residue at position 112 of SEQ ID NO: 2 and a serine residue substituted for the proline residue at position 128 of SEQ ID NO: 2, and wherein said fragment of said FGF-2 comprises at least residue numbers 30-110 of SEQ ID NO: 2.

2. The method of claim 1, further comprising the step of administering to said human patient about 10 U/kg to 80 U/kg of heparin within 30 minutes of administering said recombinant FGF-2 or said fragment of said FGF-2.

3. The method of claim 2, wherein said therapeutically effective amount of said recombinant FGF-2 or said fragment of said FGF 2 is administered into one or more coronary vessels.

4. The method of claim 3, wherein said therapeutically effective amount of said recombinant FGF-2 or said fragment of said FGF 2 is about 24 µg/kg to 48 µg/kg.

5. The method of claim 2 wherein said therapeutically effective amount of said recombinant FGF-2 or said fragment of said FGF 2 is administered into a peripheral vein.

6. The method of claim 5, wherein said therapeutically effective amount of said recombinant FGF-2 or said fragment of said FGF 2 is about 18 µg/kg to 36 µg/kg.

7. The method of claim 1, wherein said therapeutically effective amount of said recombinant FGF-2 or said fragment of said FGF 2 is administered by infusion.

8. A method for treating a human patient for coronary artery disease, comprising:
administering a single unit dose of a recombinant fibroblast growth factor-2 (FGF-2) or an angiogenically active, terminally truncated fragment of said FGF-2 into one or more coronary vessels or into a peripheral vein in a human patient in need of treatment for coronary artery disease, said unit dose comprising from about 0.008 mg to 7.2 mg of said recombinant FGF-2 or said fragment of said FGF-2;
wherein said recombinant FGF-2 is human FGF-2 and has the amino acid sequence set forth in SEQ ID NO:2 with a threonine residue substituted for the serine residue at position 112 of SEQ ID NO:2 and a serine residue substituted for the proline residue at position 128 of SEQ ID NO:2, and wherein said fragment of said FGF-2 comprises at least residue numbers 30-110 of SEQ ID NO: 2.

9. The method of claim 8, wherein said single unit dose produces a therapeutic benefit against coronary artery disease in said human patient that lasts at least four months.

10. The method of claim 9, wherein said therapeutic benefit in said human patient lasts 6 months.

11. The method of claim 10, wherein said therapeutic benefit is of such magnitude and duration in said human patient such that administration of a second unit dose is not required for about 6 months.

12. The method of claim 10, wherein said unit dose comprises 0.3 mg to 3.5 mg of said recombinant FGF-2 or said fragment of said FGF 2.

13. The method of claim 8, further comprising the step of administering 10 U/kg to 80 U/kg of heparin to said patient within 30 minutes of administering said unit dose, wherein said heparin is administered by intravenous or intracoronary administration.

14. The method of claim 8, wherein said unit dose is administered by infusion.

15. A method for treating a human patient for coronary artery disease, comprising:
administering a therapeutically effective amount of a mutein of a recombinant fibroblast growth factor-2 (FGF-2) into one or more coronary vessels or into a peripheral vein in a human patient in need of treatment for said coronary artery disease, wherein said therapeutically effective amount is about 0.2 µg/kg to 48 µg/kg of patient weight;
wherein said recombinant FGF-2 is human FGF-2 and has the amino acid sequence set forth in SEQ ID NO: 2 with a threonine residue substituted for the serine residue at position 112 of SEQ ID NO: 2 and a serine residue substituted for the proline residue at position 128 of the FGF-2 of SEQ ID NO: 2, and wherein the amino acid sequence of said mutein has at least 90% sequence identity to residues 1-146 of SEQ ID NO: 2, and wherein said mutein has angiogenic activity.

16. The method of claim 15, further comprising the step of administering to said human patient about 10 U/kg to 80 U/kg of heparin within 30 minutes of administering said mutein of said recombinant FGF-2.

17. The method of claim 16, wherein said therapeutically effective amount of said mutein of said recombinant FGF-2 is administered into one or more coronary vessels.

18. The method of claim 17, wherein said therapeutically effective amount of said mutein of said recombinant FGF-2 is about 24 µg/kg to 48 µg/kg.

19. The method of claim 16 wherein said therapeutically effective amount of said mutein of said recombinant FGF-2 is administered into a peripheral vein.

20. The method of claim 19, wherein said therapeutically effective amount of said mutein of said recombinant FGF-2 is about 18 µg/kg to 36 µg/kg.

21. The method of claim 15, wherein said therapeutically effective amount of said mutein of said recombinant FGF-2 is administered by infusion.

22. A method for treating a human patient for coronary artery disease, comprising:
administering a single unit dose of a mutein of a recombinant fibroblast growth factor-2 (FGF-2) into one or more coronary vessels or into a peripheral vein in a human patient in need of treatment for coronary artery disease, said unit dose comprising from about 0.008 mg to 7.2 mg of said mutein of said recombinant FGF-2;
wherein said recombinant FGF-2 is human FGF-2 and has the amino acid sequence set forth in SEQ ID NO: 2 with a threonine residue substituted for the serine residue at position 112 of SEQ ID NO: 2 and a serine residue substituted for the proline residue at position 128 of SEQ ID NO: 2, and wherein the amino acid sequence of said mutein has at least 90% sequence identity to residues 1-146 of SEQ ID NO: 2, and wherein said mutein has angiogenic activity.

23. The method of claim 22, wherein said single unit dose produces a therapeutic benefit against coronary artery disease in said human patient that lasts at least four months.

24. The method of claim 23, wherein said therapeutic benefit in said human patient lasts 6 months.

25. The method of claim 24, wherein said therapeutic benefit is of such magnitude and duration in said human patient such that administration of a second unit dose is not required for about 6 months.

26. The method of claim 24, wherein said unit dose comprises 0.3 mg to 3.5 mg of said mutein of said recombinant FGF-2.

27. The method of claim 22, further comprising the step of administering 10 U/kg to 80 U/kg of heparin to said patient within 30 minutes of administering said unit dose, wherein said heparin is administered by intravenous or intracoronary administration.

28. The method of claim 22, wherein said unit dose is administered by infusion.

* * * * *

UNITED STATES PATENT AND TRADEMARK OFFICE
CERTIFICATE OF CORRECTION

| | | |
|---|---|---|
| PATENT NO. | : 8,796,211 B2 | |
| APPLICATION NO. | : 13/088132 | |
| DATED | : August 5, 2014 | |
| INVENTOR(S) | : Whitehouse | |

It is certified that error appears in the above-identified patent and that said Letters Patent is hereby corrected as shown below:

<u>On the Title Page, Item (54), and in the Specification, Col. 1</u> please delete "Method of Treating Coronary Artery Disease FGF-2" and insert

--Method of Treating Coronary Artery Disease with FGF-2-- therefor.

<u>On the Title Page</u> item (63), Related U.S. Application Data, line 2, please delete "and a continuation of" and insert --which is a continuation of-- therefor.

Signed and Sealed this
Eleventh Day of November, 2014

Michelle K. Lee
*Deputy Director of the United States Patent and Trademark Office*